(12) United States Patent
Rao

(10) Patent No.: US 8,252,526 B2
(45) Date of Patent: Aug. 28, 2012

(54) SHRNA MOLECULES AND METHODS OF USE THEREOF

(75) Inventor: Donald Rao, Dallas, TX (US)

(73) Assignee: Gradalis, Inc., Carrollton, TX (US)

(*) Notice: Subject to any disclaimer, the term of this patent is extended or adjusted under 35 U.S.C. 154(b) by 0 days.

(21) Appl. No.: 11/983,482

(22) Filed: Nov. 9, 2007

(65) Prior Publication Data

US 2008/0269474 A1    Oct. 30, 2008

Related U.S. Application Data

(63) Continuation-in-part of application No. 11/601,431, filed on Nov. 17, 2006.

(60) Provisional application No. 60/932,653, filed on Jun. 1, 2007, provisional application No. 60/897,214, filed on Jan. 24, 2007, provisional application No. 60/857,846, filed on Nov. 9, 2006.

(51) Int. Cl.
| | |
|---|---|
| C12Q 1/68 | (2006.01) |
| C12P 19/34 | (2006.01) |
| C12N 15/63 | (2006.01) |
| C07H 21/02 | (2006.01) |
| C07H 21/04 | (2006.01) |

(52) U.S. Cl. ......................................................... 435/6

(58) Field of Classification Search ............. 435/6, 91.1, 435/91.31, 455, 458; 514/44; 536/23.1, 536/24.5, 24.3
See application file for complete search history.

(56) References Cited

U.S. PATENT DOCUMENTS

| | | | |
|---|---|---|---|
| 6,506,559 B1 * | 1/2003 | Fire et al. .................... | 435/6 |
| 7,763,722 B2 | 7/2010 | Chang et al. | |
| 2003/0138407 A1 | 7/2003 | Lu et al. | |
| 2003/0148295 A1 | 8/2003 | Wan et al. | |
| 2004/0023390 A1 | 2/2004 | Davidson et al. | |
| 2004/0213764 A1 | 10/2004 | Wold et al. | |
| 2004/0241854 A1 | 12/2004 | Davidson et al. | |
| 2005/0043263 A1 | 2/2005 | Giese et al. | |
| 2005/0080031 A1 | 4/2005 | McSwiggen | |
| 2005/0142578 A1 | 6/2005 | Usman et al. | |
| 2005/0143333 A1 | 6/2005 | Richards et al. | |
| 2006/0287260 A1 * | 12/2006 | Manoharan et al. ............ | 514/44 |
| 2009/0208514 A1 | 8/2009 | Nakamura et al. | |

FOREIGN PATENT DOCUMENTS

| | | | |
|---|---|---|---|
| WO | WO 02/44321 | * | 6/2002 |
| WO | WO 03/006477 | * | 1/2003 |

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Paroo et al., Trends in Biotech., vol. 22, No. 8, pp. 390-394 (2004).*
Carette, Jan E., et al., "Conditionally Replicating Adenoviruses Expressing Short Hairpin RNAs Silence the Expression of a Target Gene in Cancer Cells," Cancer Research, Apr. 15, 2004, pp. 2663-2667.
Petricoin, Emanuel F., et al., "Clinical Proteomics: Translating Benchside Promise into Bedside Reality," Nature Reviews, vol. 1, Sep. 2002, pp. 683-695.
Shen, Juqiao, et al., "Individualised Cancer Therapeutics: Dream or Reality? Therapeutics Construction," Expert Opinion, Biol. Ther. (2005) pp. 1427-1441.
Welsh, John B., et al., "Analysis of Gene Expression Profiles in Normal and Neoplastic Ovarian Tissue Samples Identifies Candidate Molecular Makers of Epithelial Ovarian Cancer," PNAS, Jan. 30, 2001, vol. 98, No. 3, pp. 1176-1181.

* cited by examiner

Primary Examiner — Jane Zara
(74) Attorney, Agent, or Firm — Edwin S. Flores; Chalker Flores, LLP

(57) ABSTRACT

The present invention relates to certain novel shRNA molecules and methods of use thereof. According to certain embodiments of the present invention, methods for reducing the expression level of a target gene are provided. Such methods generally comprise providing a cell with one or more precursor nucleic acid sequences that encode two or more RNA molecules. A first RNA molecule comprises a double stranded sequence, which includes a guide strand sequence that is complementary to a portion of an mRNA transcript encoded by the target gene. In addition, a second RNA molecule comprises a second double stranded sequence, which includes a second guide strand sequence that is partially complementary to a portion of the mRNA transcript encoded by the target gene. Preferably, the second guide strand sequence comprises one or more bases that are mismatched with a nucleic acid sequence of the mRNA transcript encoded by the target gene.

15 Claims, 18 Drawing Sheets

| ▨ SENSE SEQUENCE | ◩ ANTI-SENSE SEQUENCE | ⊞ MISMATCHES |

17/18
SENSE SEQUENCE ON THE ASCENDING STRAND.
COMPLETE MATCH SEQUENCE ON BOTH STRANDS.
dG = -23.1

AAGGATCCTGCTGTTGACAGTGAGCGC ⎡GGCACAAATGGCTGCCAAAT⎤ AGTGAAGCCACAGA

TGTA ⎡TTTGGCAGCCATTTGTGCC⎤ TTGCCTACTGCCTCGGAAGCTTTG (SEQ ID NO: 23)

---

54/18
SENSE SEQUENCE ON THE ASCENDING STRAND.
TWO NUCLEOTIDE BULGE MISMATCHES AT THE SENSE STRAND.
dG = -14.8

AAGGATCCTGCTGTTGACAGTGAGCGC ⎡GGCACAAATG⎤ ⎡AT⎤ ⎡TGCCAAAT⎤ AGTGAAGCCACAGA

TGTA ⎡TTTGGCAGCCATTTGTGCC⎤ TTGCCTACTGCCTCGGAAGCTTTG (SEQ ID NO: 24)

---

55/18
SENSE SEQUENCE ON THE ASCENDING STRAND. TWO NUCLEOTIDE BULGE
MISMATCHES PLUS ONE SINGLE BASE MISMATCH AT THE SENSE STRAND.
dG = -10.9

AAGGATCCTGCTGTTGACAGTGAGCGC ⎡GG⎤ ⎡T⎤ ⎡ACAAATG⎤ ⎡AT⎤ ⎡TGCCAAAT⎤ AGTGAAGCCACAGA

TGTA ⎡TTTGGCAGCCATTTGTGCC⎤ TTGCCTACTGCCTCGGAAGCTTTG (SEQ ID NO: 25)

---

56/18
SENSE SEQUENCE ON THE ASCENDING STRAND. TWO NUCLEOTIDE BULGE
MISMATCHES PLUS TWO SINGLE BASE MISMATCHES AT THE SENSE STRAND.
dG = -7

AAGGATCCTGCTGTTGACAGTGAGCGC ⎡GG⎤ ⎡T⎤ ⎡ACAAATG⎤ ⎡AT⎤ ⎡TG⎤ ⎡A⎤ ⎡CAAAT⎤ AGTGAAGC

CACAGATGTA ⎡TTTGGCAGCCATTTGTGCC⎤ TTGCCTACTGCCTCGGAAGCTTTG (SEQ ID NO: 26)

---

17/19
SENSE SEQUENCE ON THE ASCENDING STRAND.
TWO NUCLEOTIDE BULGE MISMATCHES AT THE ANTI-SENSE STRAND.

AAGGATCCTGCTGTTGACAGTGAGCGC ⎡GGCACAAATGGCTGCCAAAT⎤ AGTGAAGCCACAGA

TGTA ⎡TTTGGCA⎤ ⎡TA⎤ ⎡CATTTGTGCC⎤ TTGCCTACTGCCTCGGAAGCTTTG (SEQ ID NO: 27)

FIG. 3B
FROM FIG. 3A

| SENSE SEQUENCE | ANTI-SENSE SEQUENCE | MISMATCHES |

17/20
SENSE SEQUENCE ON THE ASCENDING STRAND. TWO NUCLEOTIDE BULGE
MISMATCHES PLUS A SINGLE BASE MISMATCH AT THE ANTI-SENSE STRAND.

AAGGATCCTGCTGTTGACAGTGAGCGC GGCACAAATGGCTGCCAAAT AGTGAAGCCACAGA

TGTA TTTG A CA TA CATTTGTGCC TTGCCTACTGCCTCGGAAGCTTTG (SEQ ID NO: 28)

17/21
SENSE SEQUENCE ON THE ASCENDING STRAND. TWO NUCLEOTIDE BULGE
MISMATCHES PLUS TWO SINGLE BASE MISMATCHES AT THE ANTI-SENSE STRAND.

AAGGATCCTGCTGTTGACAGTGAGCGC GGCACAAATGGCTGCCAAAT AGTGAAGCCACAGA

TGTA TTTG A CA TA CATTT A TGCC TTGCCTACTGCCTCGGAAGCTTTG (SEQ ID NO: 29)

15/16
ANTI-SENSE SEQUENCE ON THE ASCENDING STRAND.
COMPLETE MATCH SEQUENCE ON BOTH STRANDS.
dG = -23.0

AAGGATCCTGCTGTTGACAGTGAGCGC TTTGGCAGCCATTTGTGCC TAGTGAAGCCACAGA

TGTA GGCACAAATGGCTGCCAAA TTGCCTACTGCCTCGGAAGCTTTG (SEQ ID NO: 30)

15/22
ANTI-SENSE SEQUENCE ON THE ASCENDING STRAND.
TWO NUCLEOTIDE BULGE MISMATCHES AT THE SENSE STRAND.

AAGGATCCTGCTGTTGACAGTGAGCGC TTTGGCAGCCATTTGTGCC TAGTGAAGCCACAGA

TGTA GGCACAAATG TA TGCCAAA TTGCCTACTGCCTCGGAAGCTTTG (SEQ ID NO: 31)

15/23
ANTI-SENSE SEQUENCE ON THE ASCENDING STRAND. TWO NUCLEOTIDE BULGE
MISMATCHES PLUS ONE SINGLE BASE MISMATCH AT THE SENSE STRAND.

AAGGATCCTGCTGTTGACAGTGAGCGC TTTGGCAGCCATTTGTGCC TAGTGAAGCCACAGA

TGTA GGCACAAATG TA TG T CAAA TTGCCTACTGCCTCGGAAGCTTTG (SEQ ID NO: 32)

15/24
ANTI-SENSE SEQUENCE ON THE ASCENDING STRAND. TWO NUCLEOTIDE BULGE
MISMATCHES PLUS TWO SINGLE BASE MISMATCHES AT THE SENSE STRAND.

AAGGATCCTGCTGTTGACAGTGAGCGC TTTGGCAGCCATTTGTGCC TAGTGAAGCCACAGA

TGTA GGCA T AAATG TA TG T CAAA TTGCCTACTGCCTCGGAAGCTTTG (SEQ ID NO: 33)

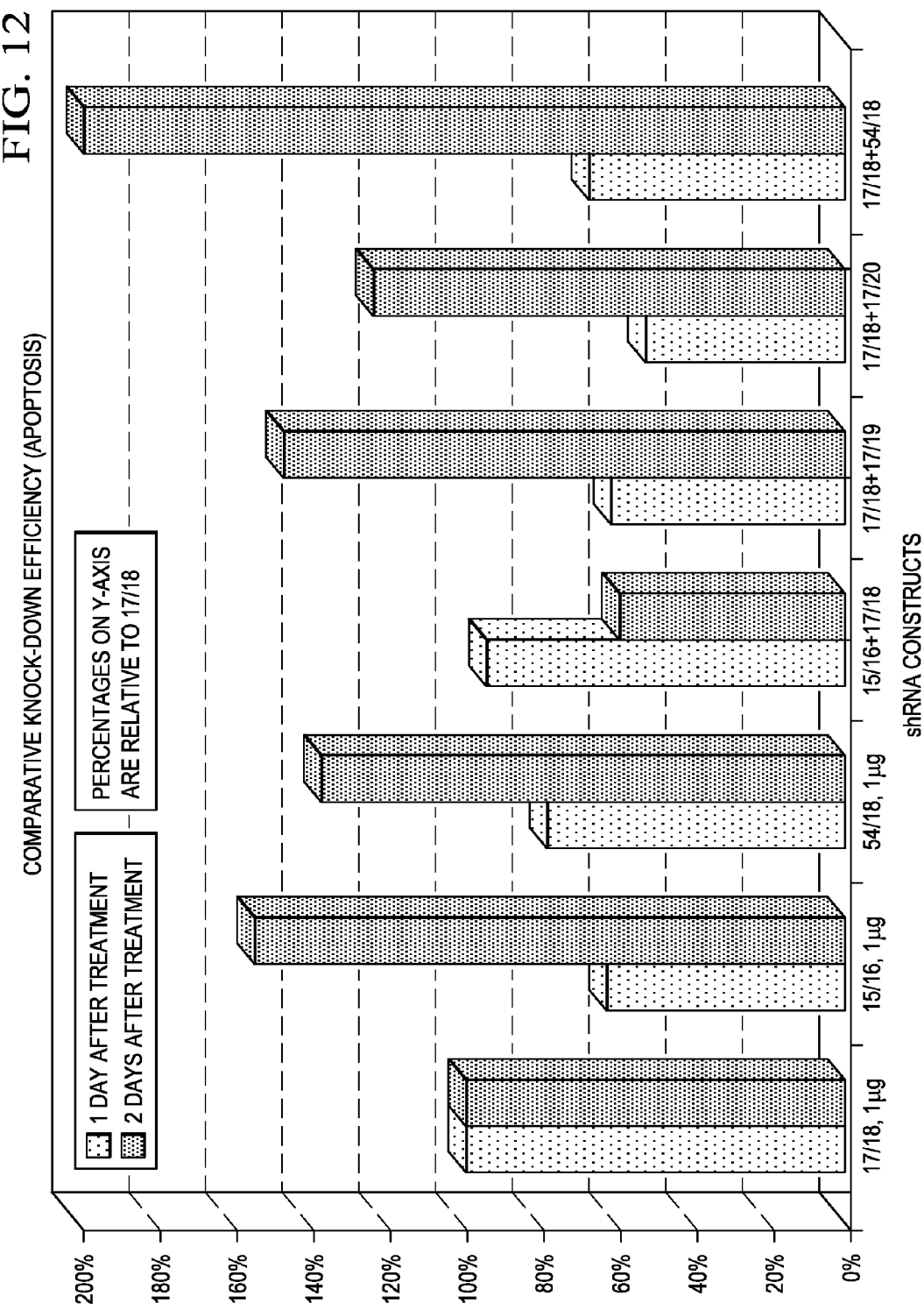

FIG. 13

| CONSTRUCT | SEQUENCE IDENTIFICATION NUMBER | SEQUENCE |
|---|---|---|
| 17/18 | 34 | AAGGATCCTGCTGTTGACAGTGAGCGC GGCACAAATGGCTGCCAAAT TTGCCTACTGCCTCGGAAGCTTTG<br>AGTGAAGCCACAGATGTA TTTGGCAGCCATTTGTGCC |
| 54/18 | 35 | AAGGATCCTGCTGTTGACAGTGAGCGC GGCACAAATG AT TGCCAAAT TTGCCTACTGCCTCGGAAGCTTTG<br>AGTGAAGCCACAGATGTA TTTGGCAGCCATTTGTGCC |
| 17/18 + 54/18 | 39 | GGATCCTGCTGTTGACAGTGAGCGC GGCACAAATGGCTGCCAAAT TTGCCTACTGCCTCGGAGATC<br>AGTGAAGCCACAGATGTA TTTGGCAGCCATTTGTGCC<br>CTGCTGTTGACAGTGAGCGC GGCACAAATG AT TGCCAAAT TTGCCTACTGCCTCGGAAGCTT<br>AGTGAAGCCACAGATGTA TTTGGCAGCCATTTGTGCC |

SENSE SEQUENCE   ANTI-SENSE SEQUENCE   MISMATCHES

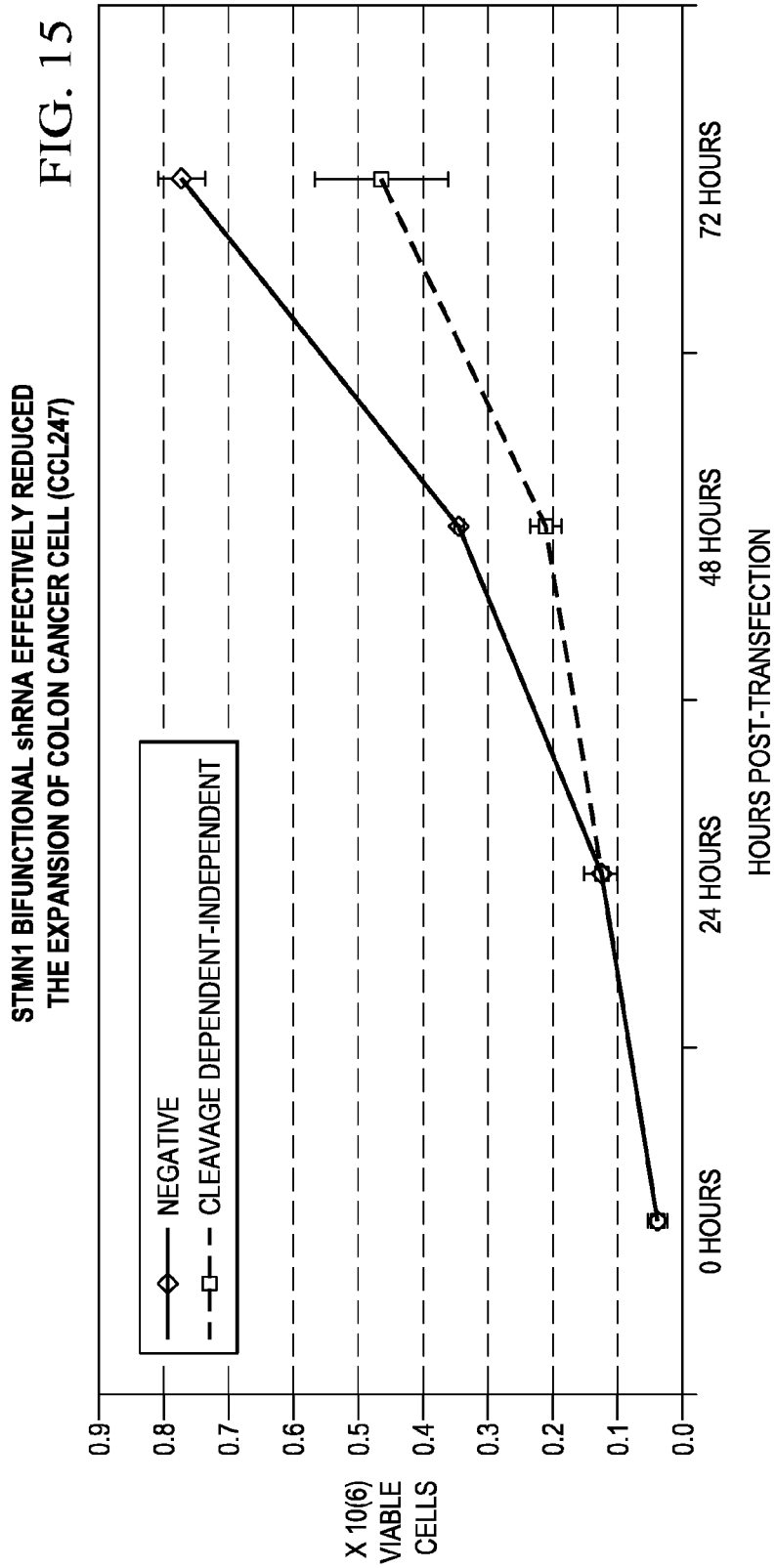

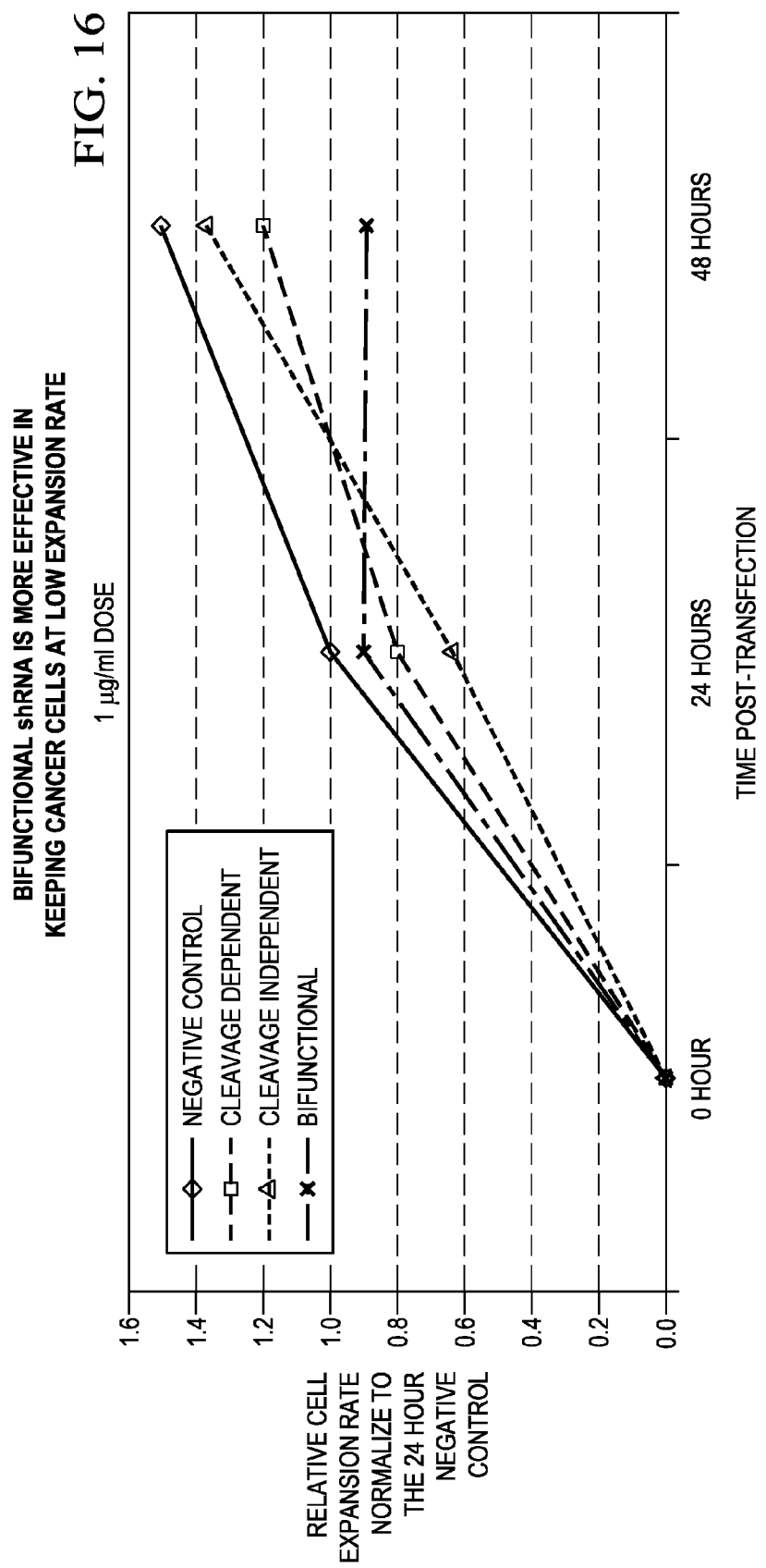

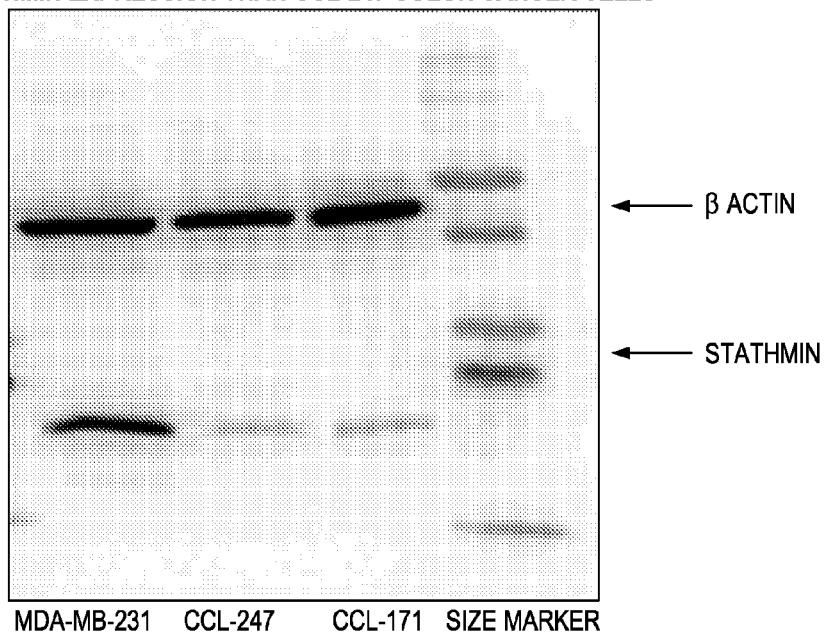
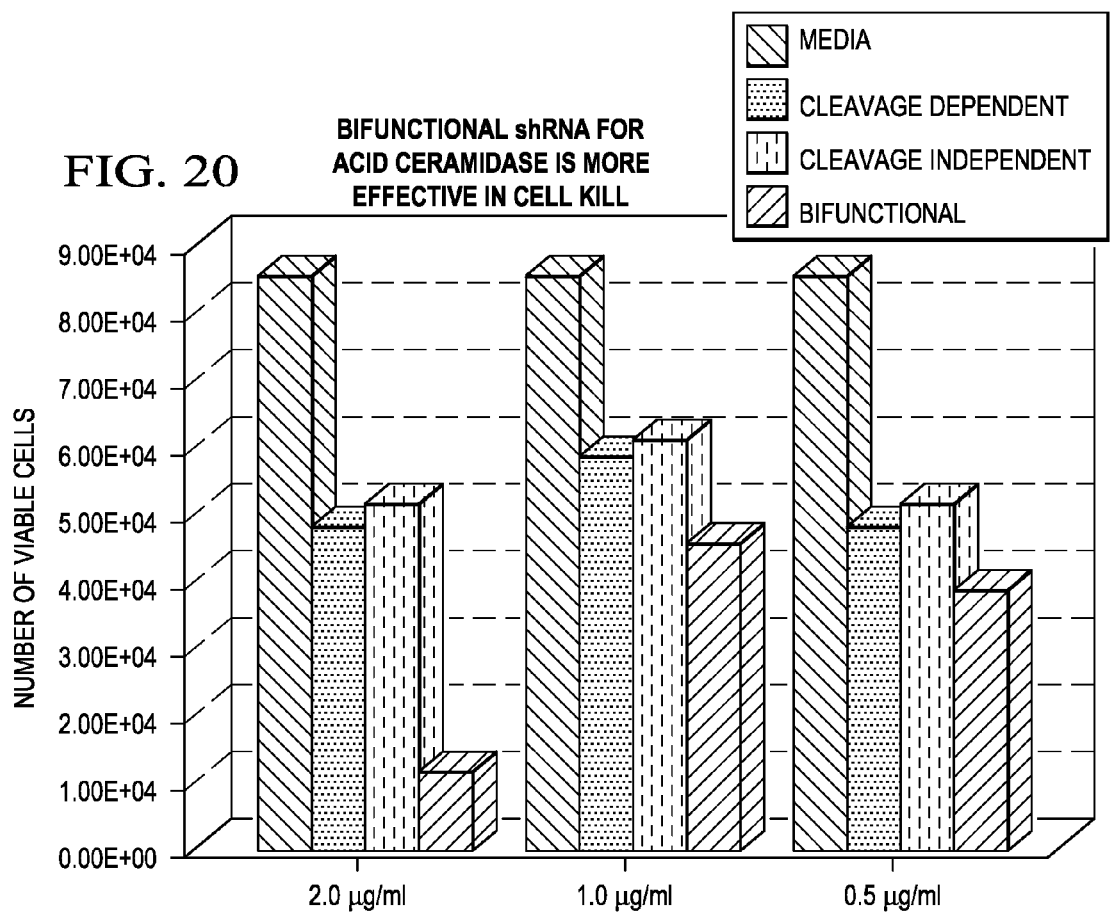

SHRNA MOLECULES AND METHODS OF USE THEREOF

CROSS-REFERENCE TO RELATED APPLICATIONS

This patent application is a continuation-in-part of, claims priority to, and incorporates by reference U.S. patent application Ser. No. 11/601,431, filed Nov. 17, 2006. This patent application further claims priority to, and incorporates by reference, U.S. provisional patent application Ser. No. 60/932,653, filed Jun. 1, 2007; Ser. No. 60/897,214, filed Jan. 24, 2007; and Ser. No. 60/857,846, filed Nov. 9, 2006.

FIELD OF THE INVENTION

The field of the present invention relates to molecular biology. More particularly, the field of the present invention relates to certain novel shRNA molecules and methods of use thereof.

BACKGROUND OF THE INVENTION

The introduction of artificial double-stranded small interfering RNAs (siRNAs) into animal and plant cells has been shown to induce the degradation of targeted mRNA molecules with homologous sequences. The use of siRNAs in such manner is a type of process that is generally known as RNA interference (RNAi). RNAi has emerged as a useful experimental tool with strong potential for therapeutic applications. However, in mammalian cells, induction of RNAi requires the transfection of RNA oligonucleotides, which can be inefficient and often gives rise to only a transient inhibition of target gene expression.

Another type of RNAi involves the use of short hairpin RNAs (shRNAs). shRNAs consist of a stem-loop structure that can be transcribed in cells from an RNA polymerase II or RNA polymerase III promoter on a plasmid construct. It has been shown that expression of shRNA from a plasmid can be stably integrated for constitutive expression, which may provide certain advantages over synthetic siRNA. shRNAs, as opposed to siRNAs, are synthesized in the nucleus of cells, further processed and transported to the cytoplasm, and then incorporated into the RNA-induced silencing complex (RISC) for activity.

The Argonaute family of proteins is the major component of RISC. Within the Argonaute family of proteins, only Ago2 contains endonuclease activity that is capable of cleaving and releasing the passenger strand from the stem portion of the shRNA molecule. The remaining three members of Argonaute family, Ago1, Ago3 and Ago4, which do not have identifiable endonuclease activity, are also assembled into RISC and are believed to function through a cleavage-independent manner. Thus, RISC can be characterized as having cleavage-dependent and cleavage-independent pathways.

The recently discovered micro-RNA (miRNA) is a new class of endogenous RNA interference molecule that is synthesized in the nucleus in a form mirrored by shRNA. This new class of short, single-stranded miRNAs are found both in plant and animal cells, and are derived from larger precursors that form a predicted RNA stem-loop structure. These miRNA precursor molecules are transcribed from autonomous promoters—or are instead contained within longer RNAs. More than 300 distinct miRNAs have been discovered to date, some of which have been found to be expressed in organisms as diverse as nematodes. miRNAs appear to play a role in the regulation of gene expression, primarily at the post-transcriptional level via translation repression. Several miRNAs have been shown to be evolutionarily conserved from *C. elegans* to man.

Like mRNAs, miRNAs are initially transcribed by RNA polymerase II into a long primary transcript (pri-miRNA) that contains one or more hairpin-like stem-loop shRNA structures. The stem-loop shRNA structures within the pri-miRNA are further processed in the nucleus by the RNase III enzyme Drosha and its cofactor DGCR-8 into pre-miRNA. Pre-miRNA is transported to the cytoplasm by the transport receptor complex Exportin-5-RanGTP, where it interacts with a second RNase III enzyme Dicer and its cofactor TRBP. Dicer trims off the loop and presents the remaining double stranded stem to the RISC to seek-out target mRNA for down regulation.

While siRNAs, shRNAs, and miRNAs have been used to suppress the expression of certain target genes with moderate success, a need exists for improved versions of RNAi molecules. Preferably, such RNAi molecules will exhibit an improved ability to suppress the expression level of target genes (i.e., improved efficacy) and, furthermore, will be capable of suppressing gene expression over a longer period of time.

SUMMARY OF THE INVENTION

According to certain aspects of the present invention, methods for reducing the expression level of a target gene are provided. Such methods generally comprise providing a cell with one or more precursor nucleic acid sequences that encode two or more RNA molecules. A first RNA molecule comprises a double stranded sequence, which includes a guide strand sequence that is complementary to a portion of an mRNA transcript encoded by the target gene. In addition, a second RNA molecule comprises a second double stranded sequence, which includes a second guide strand sequence that is partially complementary to a portion of the mRNA transcript encoded by the target gene. Preferably, the second guide strand sequence comprises one or more bases that are mismatched with a nucleic acid sequence of the mRNA transcript encoded by the target gene. In such embodiments, the guide strand exhibiting approximately 100% complementarity to the target gene mRNA will be presented to the cleavage-dependent RISC, whereas the guide strand exhibiting partial complementarity (with interspersed mismatches relative to the target gene mRNA) will be presented to the cleavage-independent RISC.

According to additional aspects of the present invention, nucleic acid sequences are provided, which may comprise a single contiguous sequence or multiple distinct sequences that, individually or collectively, encode two or more mRNA molecules. According to such embodiments, a first RNA molecule comprises a double stranded sequence that includes a guide strand sequence that is complementary to a portion of an mRNA transcript encoded by the target gene, whereas a second RNA molecule comprises a second double stranded sequence that includes a second guide strand sequence that is partially complementary to a portion of such mRNA transcript. Preferably, the second guide strand sequence comprises one or more bases that are mismatched with a nucleic acid sequence of the mRNA transcript encoded by the target gene.

According to further aspects of the present invention, expression vectors are provided which comprise the nucleic acid sequences of the present invention, and may be used to carry out the methods described herein. Still further, the present invention encompasses methods of using the nucleic acid sequences, and methods of use thereof, to prevent, treat and/or ameliorate the effects of one or more medical conditions, including without limitation various types of cancer.

The above-mentioned and additional aspects of the present invention are further illustrated in the Detailed Description contained herein. All references disclosed herein, including U.S. patents and published patent applications, are hereby incorporated by reference in their entirety as if each was incorporated individually.

BRIEF DESCRIPTION OF THE DRAWINGS

FIG. 3 is a diagram (and partial sequence listing) of the various shRNA constructs described in the Examples below.

FIG. 12 is another bar graph that summarizes the comparative gene silencing activity of various shRNA constructs described in the Examples below.

FIG. 13 is a table that shows the design (and partial sequence listing) of constructs 17/18 and 54/18 (and combinations thereof) as described herein.

FIG. 15 is a line graph showing that STMN1 Bifunctional shRNA is able to reduce the expansion of colon cancer cells in culture.

FIG. 16 is a line graph that compares the ability of STMN1 Bifunctional shRNA to conventional shRNA to reduce the expansion of colon cancer cells in culture.

FIG. 18 is an image of a gel showing the elevated amount of Stathmin-1 protein in the MDA-MB-231 breast cancer cell line.

FIG. 20 is a bar graph that compares the ability of Acid Ceramidase Bifunctional shRNA to conventional shRNA to induce cell kill.

BRIEF DESCRIPTION OF THE SEQUENCE LISTING

Figure 1:
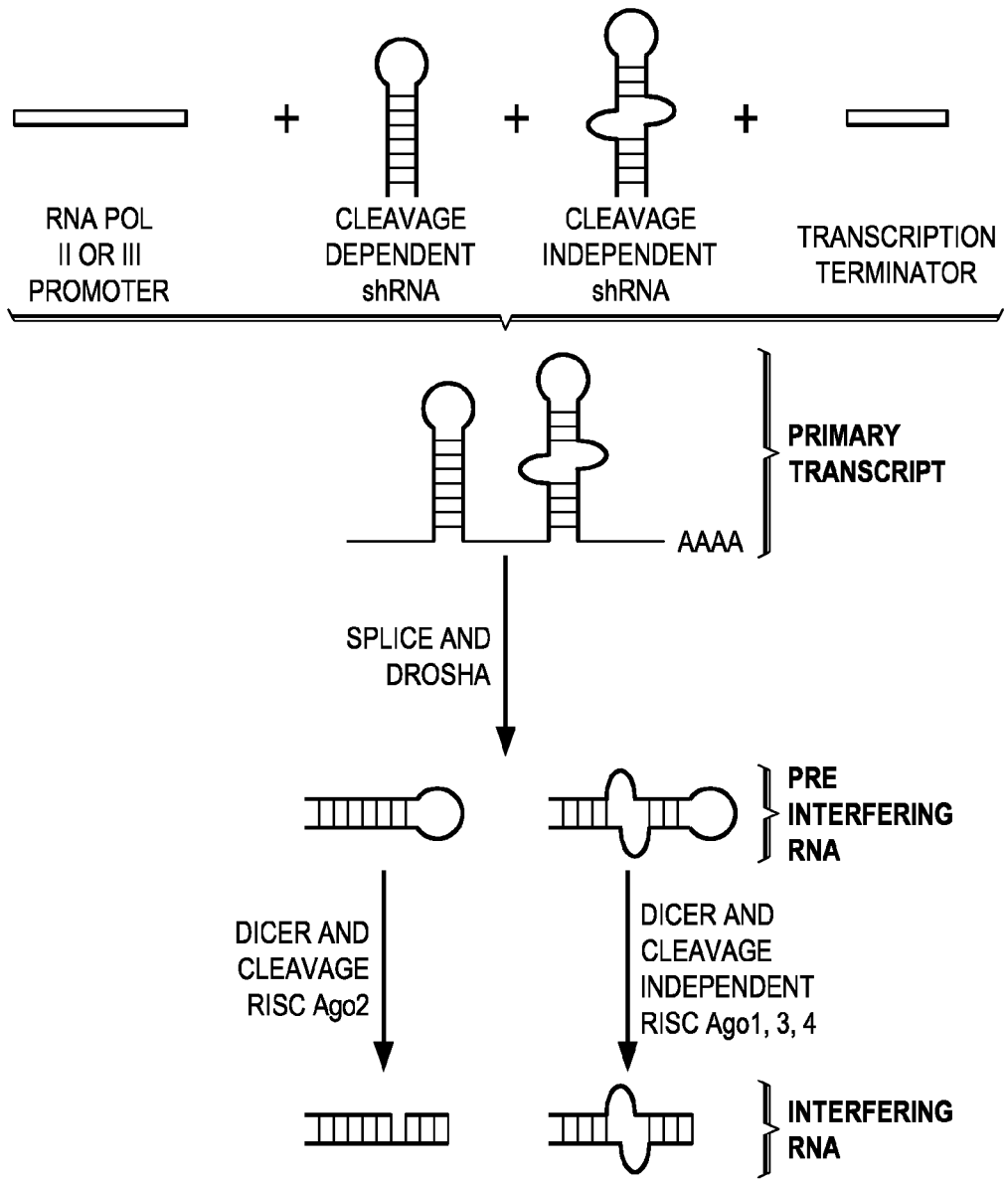
FIG. 1 is a diagram illustrating the cleavage-dependent and cleavage-independent RISC pathways described herein.

SEQ ID NOs 1-3 are PCR primer sequences used in Example 1.

SEQ ID NO 4 is the sense strand of a STMN1 siRNA molecule.

SEQ ID NO 5 is the antisense strand of a STMN1 siRNA molecule.

SEQ ID NOs 6-7 are PCR primers used with psiTEST.

SEQ ID NOs 8-9 are PCR primers used with pSilencer.

SEQ ID NOs 10-22 are the nucleic acid sequences of the shRNA constructs described in Table-1 below.

SEQ ID NOs 23-33 are the nucleic acid sequences of the shRNA constructs illustrated in FIG. 3.

SEQ ID NOs 34-35 are the nucleic acid sequences of the shRNA constructs 17/18 and 54/18, respectively.

SEQ ID NOs 36-38 are PCR primers used in the cloning procedures discussed in Example 2 below.

SEQ ID NO 39 is a nucleic acid sequence that encodes Bifunctional shRNAs that include constructs 17/18 and 54/18 within a single preliminary transcript.

SEQ ID NO 40 is a nucleic acid sequence that encodes Bifunctional shRNA that was designed to reduce the expression level of Acid Ceramidase.

SEQ ID NO 41-48 are PCR primers that were used to construct various shRNA molecules that were designed to reduce the expression level of Acid Ceramidase.

SEQ ID NO 49 is the genomic DNA sequence for Stathmin-1.

SEQ ID NO 50 is an mRNA sequence that encodes Stathmin-1.

DETAILED DESCRIPTION OF THE INVENTION

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

The present invention provides new, improved, and more efficacious shRNA molecules and methods of use thereof, which may be used to modulate the expression level of one or more target genes. In general, shRNAs consist of a stem-loop structure that may be transcribed in cells from a plasmid construct. The stem-loop structure consists of a stem portion that comprises a double stranded sequence. The double stranded stem portion comprises a guide strand on one side of the stem, and a passenger strand on the other side of the stem. The stem-loop structure further comprises a single stranded loop portion at one end of the stem. These stem-loop structures are generally illustrated in FIG. 1.

Expression of shRNA from a plasmid is known to be relatively stable, thereby providing strong advantages over, for example, the use of synthetic siRNAs. shRNA expression units may be incorporated into a variety of plasmids, liposomes, viral vectors, and other vehicles for delivery and integration into a target cell. shRNAs are synthesized in the nucleus of cells, further processed and transported to the cytoplasm, and then incorporated into the RNA-induced silencing complex (RISC) where the shRNAs are converted into active molecules (which are capable of binding to, sequestering, and/or preventing the translation of mRNA transcripts encoded by target genes).

Figure 2:
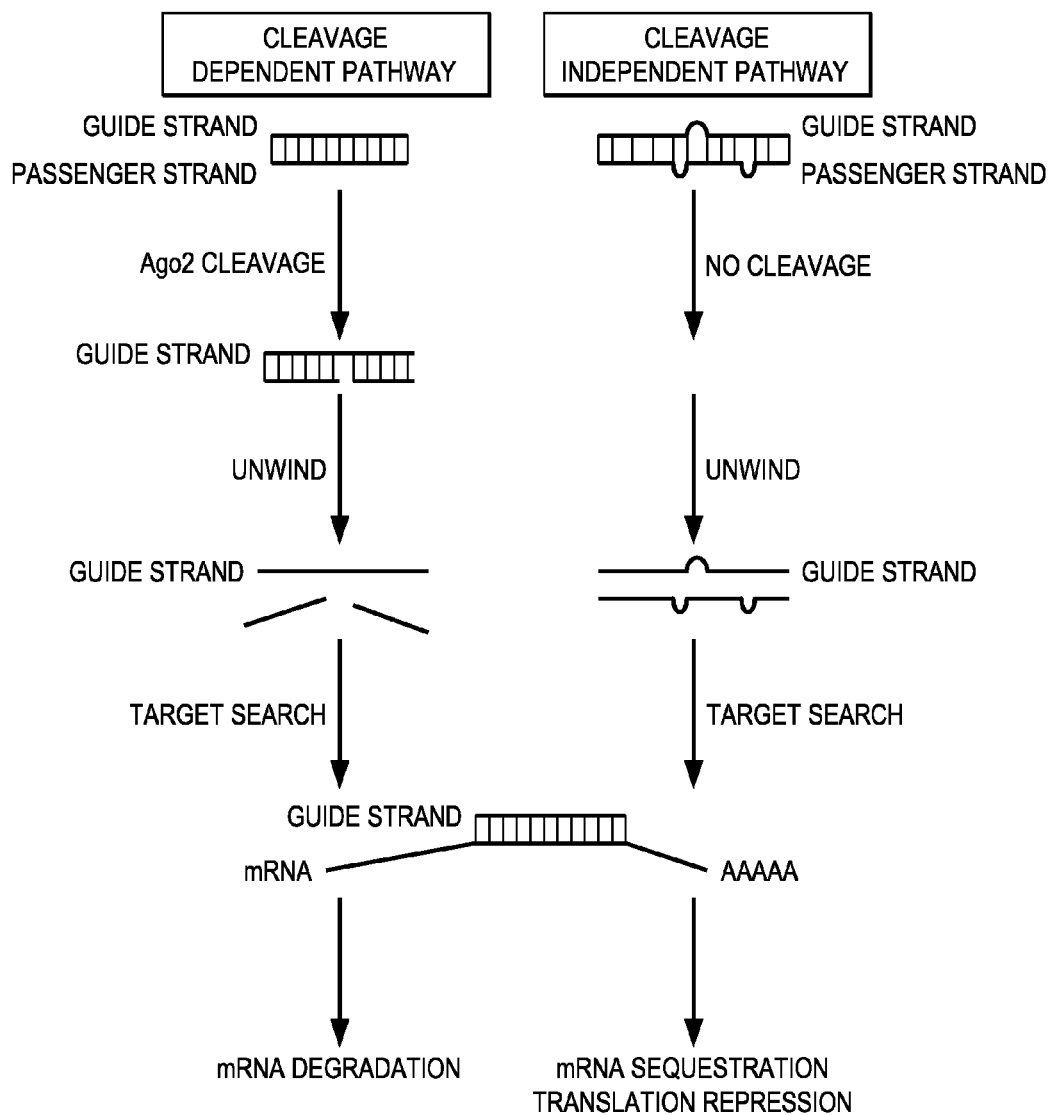
FIG. 2 is another diagram illustrating the cleavage-dependent and cleavage-independent RISC pathways described herein.

Referring to FIGS. 1 and 2, RISC may be characterized into cleavage-dependent RISC and cleavage-independent RISC. The Argonaute family of proteins is the major component of RISC. Within the Argonaute family of proteins, only Ago2 contains endonuclease activity that is capable of cleaving and releasing the passenger strand from the double stranded stem. The remaining three members of the Argonaute family, Ago1, Ago3 and Ago4, which do not have identifiable endonuclease activity, are also assembled into RISC and are believed to function through a cleavage-independent manner. Thus, RISC can be characterized as having cleavage-dependent and cleavage-independent pathways.

The invention provides that target gene-specific shRNAs may be designed to enter into and interact with the cleavage-dependent RISC and cleavage-independent RISC pathways. As used herein, the term "Bifunctional shRNA" generally means two or more RNA molecules, each of which include a double stranded sequence that resides within a stem portion of separate stem-loop structures, wherein a first RNA molecule is designed to be presented to a cleavage-dependent RISC pathway and a second RNA molecule is designed to be presented to a cleavage-independent RISC pathway.

More specifically, referring to FIGS. 1 and 2, a first RNA molecule includes a guide strand sequence that is complementary, preferably 100% complementary, to at least a portion of an mRNA transcript encoded by a target gene. The invention provides that this guide strand (which is initially bonded to the passenger strand to form the double stranded stem) comprises a nucleic acid sequence that is capable of binding to the mRNA transcript of the target gene, and is presented to the cleavage-dependent RISC pathway. The invention provides that such binding of the guide strand sequence to the mRNA transcript, and presentation to the cleavage-dependent RISC pathway, causes degradation of the mRNA transcript. This is generally illustrated in FIGS. 1 and 2.

The invention further provides that the second RNA molecule also includes a guide strand sequence which is at least partially complementary to at least a portion of the mRNA transcript encoded by the target gene. More particularly, the invention provides that the guide strand sequence of the second RNA molecule will contain a first portion that is complementary, preferably 100% complementary, to the mRNA transcript encoded by the target gene, whereas a second portion of the guide strand sequence of the second RNA molecule will contain certain bases that are "mismatched" with the corresponding sequence of the target gene mRNA transcript.

As used herein, a "mismatched" base pair refers to two nitrogenous bases within a nucleic acid sequence that, when bound (or hybridized) to each other, do not follow Chargaff's rules of base pairing. Chargaff's rules provide that the purine adenine (A) within a first nucleic acid sequence will pair with the pyrimidine thymine (T) (or uridine (U)) within a second nucleic acid sequence. Furthermore, Chargaff's rules provide that the purine guanine (G) within a first nucleic acid sequence will pair with the pyrimidine cytosine (C) within a second nucleic acid sequence. Thus, a base pairing between two strands (nucleic acid sequences) that does not follow and comply with such rules would be deemed a "mismatched" base pair, e.g., a pairing between G and U, A and G, A and C, G and T, G and U, and so on. As generally illustrated in FIGS. 1 and 2, a guide strand within the double stranded sequence of the stem-loop structures shown therein, which contain one or more "mismatched" base pairs relative to the passenger strand, creates a bulge in the double stranded stem sequence.

The invention provides that the second RNA molecule, which includes a guide strand sequence that is partially complementary to at least a portion of the target gene mRNA transcript and contains one or more bases that are "mismatched" with the corresponding sequence of the target gene mRNA transcript, will be presented to the cleavage-independent RISC pathway. This is also generally illustrated in FIGS. 1 and 2. The guide strand of the second RNA molecule will preferably be capable of sequestering the mRNA transcript encoded by the target gene, thereby repressing the translation thereof.

Accordingly, the Bifunctional shRNAs encompassed by, and employed in, the present invention comprise shRNAs designed to enter into and interact with both cleavage-dependent RISC and cleavage-independent RISC. The invention provides that a higher level of gene "knock-down" is achieved using such Bifunctional shRNAs than other currently-available RNAi methods and compositions, including siRNAs and conventional shRNAs (i.e., shRNA constructs designed to enter cleavage-dependent RISC or cleavage-independent RISC, but not both). As used herein, gene "knock-down" refers to effective quantitative and durable inhibition of expression. Such gene "knock-down" may be manifested, and/or apparent, in the suppression of target gene mRNA translation, increased target cell apoptosis and/or cell kill.

According to certain embodiments, the invention provides methods and compositions for the synthesis of the Bifunctional shRNA molecules described herein, which may be transcribed endogenously in human, animal and plant cells, for the purpose of "knocking down" (or reducing, silencing, or effectively eliminating) the expression of one or more target genes. More specifically, according to certain aspects of the present invention, methods for reducing the expression level of a target gene are provided that generally comprise providing a cell with one or more precursor nucleic acid sequences that encode two or more RNA molecules, which together constitute the Bifunctional shRNA described herein. More specifically, a first RNA molecule will comprise a double stranded sequence (a stem), which includes a guide strand sequence that is complementary, preferably 100% complementary, to a portion of an mRNA transcript encoded by the target gene. In addition, a second RNA molecule comprises a second double stranded sequence (a stem), which includes a second guide strand sequence that is partially complementary to a portion of the mRNA transcript encoded by the target gene. The second guide strand sequence will preferably comprise one or more bases that are mismatched with a nucleic acid sequence of the mRNA transcript encoded by the target gene. In certain embodiments, it is preferred that the second guide strand be designed to be perfectly (about 100%) complementary to the target gene mRNA transcript at positions 2-8 of the stem, such that the one or more mismatched base pairs are interspersed following position 8 of the stem.

Accordingly, a first aspect of the Bifunctional shRNAs will, preferably, promote the cleavage of mRNAs bearing a fully complementary target site, while a second aspect of the Bifunctional shRNAs will, preferably, inhibit expression of mRNAs bearing partially complementary sequences (without necessarily inducing cleavage). The invention provides that simultaneous expression of both aspects of the Bifunctional shRNAs in cells establishes conditions within effected cells such that RNA interference may be activated through cleavage-dependent and cleavage-independent pathways. The invention further provides that the Bifunctional shRNAs may be designed so as to target 3' or 5' untranslated regions of target gene mRNA transcripts or coding regions thereof.

As used herein, "target gene" refers to a nucleic acid sequence in a cell, wherein the expression of the sequence may be specifically and effectively modulated using the Bifunctional shRNAs and methods described herein. In certain embodiments, the target gene may be implicated in the growth (proliferation), maintenance (survival), and/or migratory (metastatic) behavior of an individual's cancer. The invention provides, however, that the target gene may be implicated in any other disease or medical condition, and is not limited to genes implicated in cancer. For example, the target gene may represent any sequence that an investigator or clinician wishes to silence (i.e., reduce the expression level of such target gene).

The precursor nucleic acid sequences (or constructs) that may be used to encode the Bifunctional shRNAs described herein may comprise a promoter, which is operably linked (or connected), directly or indirectly, to a sequence encoding the Bifunctional shRNAs. Such promoters may be selected based on the host cell and the effect sought. Non-limiting examples of suitable promoters include constitutive and inducible promoters, such as inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The invention shall not be restricted to the use of any single promoter, especially since the invention may comprise two or more Bifunctional-shRNAs (i.e., a combination of effectors), including but not limited to incorporated shRNA singlets. Each incorporated promoter may control one, or any combination of, the shRNA singlet components.

In certain embodiments, the promoter may be preferentially active in the targeted cells, e.g., it may be desirable to preferentially express the Bifunctional shRNA molecules in tumor cells using a tumor cell-specific promoter. Introduction of such constructs into host cells may be effected under conditions whereby the two or more RNA molecules that are contained within the Bifunctional shRNA precursor transcript initially reside within a single primary transcript, such that the separate RNA molecules (each comprising its own stem-loop structure) are subsequently excised from such precursor transcript by an endogenous ribonuclease. The invention further provides that splice donor and acceptor sequences may be strategically placed within the primary transcript sequence to promote splicesome-mediated nuclear processing. The resulting mature shRNAs may then induce degradation, and/or translation repression, of target gene mRNA transcripts produced in the cell, as generally illustrated in FIGS. 1 and 2. Alternatively, each precursor stem-loop structure may be produced as part of a separate transcript, in which case each shRNA-encoding sequence will preferably include its own promoter and transcription terminator sequences. Additionally, the Bifunctional shRNA precursor transcript may reside within a single primary transcript, which, optionally, further comprises of one or more mRNA sequences that encode one or more functional mammalian proteins. For example, the one or more mRNA sequences may encode certain proteins that are known to bolster a patient's immune system, or otherwise provide some preventative and/or therapeutic effect that will operate in parallel with the Bifunctional shRNA.

The stem-loop structures of the shRNA molecules described herein may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail), however, bulges or interior loops may be present, and even preferred, on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. More particularly, the loop portion will preferably be 6-15 nucleotides in size.

As described herein, the stem regions of the Bifunctional shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.gov/BLAST).

The invention provides that the expression level of multiple target genes may be modulated using the methods and Bifunctional shRNAs described herein. For example, the invention provides that a first set of Bifunctional shRNAs may be designed to include a sequence (a guide strand) that is designed to reduce the expression level of a first target gene, whereas a second set of Bifunctional shRNAs may be designed to include a sequence (a guide strand) that is designed to reduce the expression level of a second target gene. The different sets of Bifunctional shRNAs may be expressed and reside within the same, or separate, preliminary transcripts. In certain embodiments, such multiplex approach, i.e., the use of the Bifunctional shRNAs described herein to modulate the expression level of two or more target genes, may have an enhanced therapeutic effect on a patient. For example, if a patient is provided with the Bifunctional shRNAs described herein to treat, prevent, or ameliorate the effects of cancer, it may be desirable to provide the patient with two or more types of Bifunctional shRNAs, which are designed to reduce the expression level of multiple genes that are implicated in the patient's cancer.

In certain embodiments, the invention further provides that the Bifunctional shRNA sequences may comprise stem sequences of naturally occurring miRNAs (e.g., miR-30, *C. elegans* let-7 and/or lin-4). While the presence of a miR-30 loop, for example, may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)).

The precursor sequences (or constructs) encoding the Bifunctional shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, targeted nanoparticles, targeted liposomes, cyclodextrins, nanoparticles, aptamers, dendrimers, chitosan, or pegylated derivatives thereof. The nature of the delivery vehicle may vary depending on the target host cell.

In-vivo delivery of the Bifunctional shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA)). Administration may further be achieved via syringe needles, trocars, canulas, catheters, etc., as appropriate.

In addition to the methods of using the Bifunctional shRNAs described herein, the invention further encompasses the shRNAs themselves. Accordingly, additional aspects of the present invention include nucleic acid sequences, which may comprise a single contiguous sequence or multiple distinct sequences that, individually or collectively, encode two or more RNA molecules. According to such embodiments, a first RNA molecule will comprise a double stranded sequence that includes a guide strand sequence that is complementary to a portion of an mRNA transcript encoded by a target gene, whereas a second RNA molecule comprises a second double stranded sequence that includes a second guide strand sequence that is partially complementary to a portion of such mRNA transcript. Preferably, the second guide strand sequence of the second RNA molecule comprises one or more bases that are mismatched with a nucleic acid sequence of the mRNA transcript encoded by the target gene. According to further aspects of the present invention, expression vectors are provided which comprise the nucleic acid sequences of the present invention, and may be used to carry out the methods, and express the Bifunctional shRNAs, described herein.

Still further, the present invention encompasses methods of using the nucleic acid sequences and Bifunctional shRNAs described herein to prevent, treat and/or ameliorate the effects of one or more medical conditions, including without limitation various types of cancer. For example, the invention provides that the Bifunctional shRNAs described herein may be used to reduce the expression level of one or more target genes that are implicated in cancer cell growth, survival, and/or metastasis. For example, as demonstrated in the Examples below, the Bifunctional shRNAs may be used to reduce the expression level of certain target genes that encode scaffold proteins, which have been found to be over-expressed in cancer cells. Non-limiting examples of such target genes include Stathmin-1, RACK-1, Annexin II, and others.

The Bifunctional shRNAs of the invention may further be used, for example, to reduce the expression level of pro-inflammatory genes or anti-apoptosis genes where therapeutically desirable. For example, expression of BCL-2 or acid ceramidase has been found to render tumor cells resistant to chemotherapy. Using the Bifunctional shRNAs described herein, the expression level of BCL-2 or acid ceramidase may be reduced, thereby enhancing the ability of chemotherapeutic agents to cause tumor cells to undergo senescence. Similarly, T-cells isolated from a tumor bearing patient can be modified ex-vivo using precursor sequences encoding Bifunctional shRNAs designed to reduce the expression level of the TGF-β receptor, thereby affecting the patient's immune response. Upon reintroduction into the patient, the killing ability of the T-cells will be enhanced. Likewise, T-cells can be modified ex-vivo to inhibit expression of the Fas receptor, thereby increasing the tumor killing capacity of the cells upon reintroduction.

The invention provides that the target genes can be naturally occurring sequences, transgenes or can be pathogen sequences present, for example, as a result of infection. For example, the Bifunctional shRNAs of the invention can be used to "turn off" papilloma viruses in humans (e.g., in the uterus by using an appropriately designed adeno-associated viral vector).

In addition to therapeutic applications, the Bifunctional shRNAs described herein may be used in research-oriented applications. Cultured cells suitable as hosts for the precursor sequences encoding the Bifunctional shRNAs of the present invention include both primary cells and cell lines. These cells may be human cells, including human stem cells, animal cells, plant cells, or other types of cells. A construct of the invention encoding the Bifunctional shRNAs may be introduced into cultured cells to inactivate a specific gene of unknown function. Silencing the gene of interest using the Bifunctional shRNAs can be used as an approach to assess its function. Of course, the Bifunctional shRNAs of the invention may be introduced into non-human animal cells to produce a model experimental animal. In the case of experimental animals, the Bifunctional shRNAs can be used for large scale analysis of gene function.

The following examples are provided to further illustrate the compositions and methods of the present invention. These examples are illustrative only and are not intended to limit the scope of the invention in any way.

EXAMPLES

Example 1

Expression of Bifunctional shRNAs in Separate Preliminary Transcripts

Materials and Methods

All oligonucleotides used in this Example were purchased from IDTDNA (Coralville, Iowa). Human Embryonic Kidney cells, HEK 293 cells, were obtained from ATCC (Manassas, Va.) and were grown in DMEM, and supplemented with 10% fetal bovine serum (Hyclone®) (Logan, Utah) and 2 mM L-Glutamine (Gibco BRL) (Grand Island, N.Y.). Human Colonic Carcinoma HCT116 cells (ATCC CCL247) were obtained from ATCC (Manassas, Va.) and were grown in McCoy's 5A medium with 2 mM L-Glutamine (Hyclone®) (Logan, Utah), and supplemented with 10% fetal bovine serum (Hyclone®) (Logan, Utah).

RNA isolation and cDNA production. Total cellular RNA was isolated from CCL 247 colon cancer cell line. Total cellular RNA isolation was accomplished with a RNeazy mini-kit (Qiagen)(Valencia, Calif.) by following manufacturer's recommendations. Gene specific cDNA was synthesized by RT-PCR. cDNA was first synthesized from total RNA with a gene specific primer (SEQ ID NO: 1) and Superscript III (Invitrogen) (Carlsbad, Calif.). cDNA was further amplified with gene-specific PCR primers containing Nhe I and Bgl II sites at the ends to facilitate cloning. The PCR primers used are represented by SEQ ID NO: 2 and SEQ ID NO: 3. PCR product of approximately 1350 base pairs was digested with NheI and Bgl II, and purified from a 0.8% agarose gel before ligating into a NheI and Bgl II digested psiTEST.

Reporter-gene cDNA fusion construct psiTEST was purchased from Invitrogen (San Diego, Calif.). Double stranded cDNA was digested with Nhe I and Bgl II, and ligated with NheI and Bgl II digested psiTEST for directional insertion of cDNA.

shRNA expression construct. For each shRNA construct, two sixty-nucleotide oligonucleotides with short overlapping complement sequences were purchased from IDTDNA (Coralville, Iowa). dsDNA was synthesized by a fill-in reaction with high-fidelity Taq DNA polymerase (Invitrogen) (Carlsbad, Calif.), digested with Bam HI and Hind III and the appropriate size DNA was isolated from agarose gel before insertion into the Bam HI and Hind III sites of pSilencer 4.1-CMVneo (Ambion) (Austin, Tex.).

siRNA nucleic acid sequences. siRNAs were purchased from Ambion (Austin, Tex.). The siRNA for Stathmin-1 (STMN1) (#16428) has the sequences represented by SEQ ID NO: 4 (the sense strand) and SEQ ID NO: 5 (the antisense strand). Sequence determination was performed by SeqWright (Houston, Tex.). The forward primer for psiTEST is represented by SEQ ID NO: 6, and the reverse primer for psiTEST is represented by SEQ ID NO: 7. The forward primer for pSilencer is represented by SEQ ID NO: 8, and the reverse primer for pSilencer is represented by SEQ ID NO: 9.

Transfection of cell lines with siRNA or shRNA. Reverse-transfection of cell lines was performed using siPort™, NeoFX™, or siPort™ Amine (Ambion) (Austin, Tex.) by following the protocol recommended by the manufacturer. Briefly, one hour before transfection, healthy growing adherent cells were trypsinized and resuspended in normal growth medium at $1 \times 10^5$ cells/ml. 5 µl of siPORT NeoFX was diluted into 100 µl of Opti-MEM 1 medium in each well of a 6-well plate. The plate was incubated for 10 minutes at room temperature. The siRNAs were diluted into Opti-MEM 1 medium to achieve a final concentration of 10-30 nM as required in 100 µl/well volume of OptiMEM1. The diluted siPORT NeoFX and diluted siRNA were subsequently combined. The mixture was incubated for 10 minutes at room temperature.

The transfection complexes were next dispensed into the empty 6 well plates (200 µl/well). The cells were gently mixed and provided with 2.3 ml of the $1 \times 10^5$ cell/ml concentration in each well of the 6 well plate. The plate was gently agitated to evenly distribute the complexes. The plate was then incubated at 37° C., and inspected for cytotoxicity after 8 hours. If cytotoxicity was observed, the media was replaced with fresh media. After 24 hours of incubation, the media was replaced with fresh media. The cells were analyzed, as described herein, following 24 hours, 48 hours and 4 days post-transfection for protein knock-down by Western Blot, flow cytometry and/or RT-PCR. Transfections were also performed with Lipofectamine™ 2000 (Invitrogen) (Carlsbad, Calif.) using the protocol recommended by the manufacturer.

Secreted alkaline phosphatase assay. Secreted alkaline phosphatase was assayed using the calorimetric EnzoLyte™ pNPP Secreted Alkaline Phosphatase Reporter Gene Assay Kit (AnaSpec) (San Jose, Calif.). Cell culture media was first incubated at 65° C. for 30 minutes to inactivate the endogenous non-specific alkaline phosphatase. Assays were performed in 96-well plates, 50 µl of media were used per well. Triplicate samples were used for each data point and compared against a standard concentration curve. A GraphPad Prism program was used to extrapolate the concentration in units of samples from the standard curve.

Western Immunoblotting. Cells were lysed with CellLytic-M lysis buffer (Sigma-Aldrich Co.) (Saint Louis, Mo.) and removed from the surface of the culture dish. The cells were incubated at room temperature for 30 minutes on a slow shaker and briefly centrifuged. A small aliquot was taken for protein concentration estimation by Coomassie Bradford Plus Assay (Sigma-Aldrich Co.) (Saint Louis, Mo.) with BSA as the standard. SoftMaxPro software was used to calculate the protein concentration values and plot the standard curve. Equal amounts of protein were separated on a pre-assembled gel (5-20 µg), 15% PAGE, using a Mini-Protein II Cell system (Bio-Rad).

Following electrophoresis, the separated proteins were electro-transferred onto a PVDF membrane under standard conditions. The membranes were first blocked with blocking buffer containing 5% non-fat dried milk in DPBS-T overnight at 4° C. After two changes of wash buffer, proteins were first tagged with rabbit polyclonal primary antibody to Stathmin-1 (Calbiochem-EMD) (Biosciences, Inc., La Jolla, Calif.) and then HRP-conjugated secondary antibody (Abcam) (Cambridge, Mass.). Chemiluminescent detection was performed using ECL Plus Western Blotting Detection reagents (GE HealthCare) with BioMax MR films (Kodak). Membranes were stripped and re-probed with a different antibody to detect the house keeping protein β-Actin. The membranes were scanned using an AlphaImager 2000 Digital Imaging System (Alpha Innotech Corporation). Quantitative densitometric analysis was carried out using a Beta Release 2 of Scion Image (Scion Corporation).

Flow cytometry analysis. siRNA and shRNA transfected cells were treated with trypsin and subsequently collected. An aliquot of cells were set apart for staining to evaluate and quantitate the dead and apoptotic cells. The remaining cells were fixed and permeabilized using a Fix and Perm reagent (BD Biosciences) for 20 minutes at 4° C. in the dark. Following permeabilization, the cells were incubated with primary antibody in 100 µl of staining buffer for 30 minutes at 4° C. in the dark. Fluorescein-tagged secondary antibody was added to the cells and incubated for 10 minutes. The cells were washed and stored in staining buffer for acquisition of events using FACS caliber (BD Biosciences). The data was analyzed using FACS PRO software. The percentage of dead or apoptotic cells was calculated.

Viable Cell Count by Trypan Blue Dye Exclusion. Sample cells were diluted 1:10 with DPBS and added with 50 µl of trypan blue (Trypan Blue 0.4%, Gibco BRL). Viable cells were counted with a hemacytometer.

Oligonucleotides for STMN1 shRNA constructions. Table-1 below summarizes the nucleic acid sequences of the shRNAs described in this Example.

TABLE 1

| Construct | SEQ ID NO |
|---|---|
| 15 | SEQ ID NO: 10 |
| 16 | SEQ ID NO: 11 |
| 17 | SEQ ID NO: 12 |
| 18 | SEQ ID NO: 13 |
| 19 | SEQ ID NO: 14 |
| 20 | SEQ ID NO: 15 |
| 21 | SEQ ID NO: 16 |
| 22 | SEQ ID NO: 17 |
| 23 | SEQ ID NO: 18 |
| 24 | SEQ ID NO: 19 |
| 54 | SEQ ID NO: 20 |
| 55 | SEQ ID NO: 21 |
| 56 | SEQ ID NO: 22 |

The sequences of the stem-loop structures of the Bifunctional shRNAs used in this Example are further shown in FIG. 3.

Results

Design of shRNA and expression constructs. As an example, the shRNAs were designed to target Stathmin-1 (STMN1). Stathmin-1 is a phosphorylation-regulated cytosolic protein that serves to destabilize microtubule formation and, therefore, is highly involved in the mitotic spindle formation process. Stathmin-1 is frequently over-expressed in human tumors, including acute leukemia, lymphoma, neuroblastoma, ovarian carcinoma, prostate cancer, breast cancer and lung cancer. Anti-sense depletion of STMN1 in cancer cells has been shown to inhibit cell growth by causing accumulation of cells with $G_2$/M-content DNA. As such, STMN1 was an excellent target to demonstrate efficacy of the Bifunctional shRNAs, with potential clinical applications.

In this Example, the Bifunctional shRNAs were designed to include a 15-base loop region comprising a miR-30 sequence. This modification was believed to provide more efficient Drosha processing from pri-miRNA to pre-miRNA. The stem portions of the Bifunctional shRNAs were designed to include sequences that were complementary to an mRNA transcript (SEQ ID NO: 50) encoded by the STMN1 target gene (SEQ ID NO: 49).

To test for the positional effect of the siRNA sequence, the STMN1-specific siRNA sequences were placed in both orientations either on the ascending strand or on the descending strand of the stem of the stem-loop structure. The shRNAs were designed using Constructs 15/16 and Constructs 17/18, with guiding strand (anti-sense) at the ascending strand and the descending strand of the stem-loop structure, respectively. The nucleic acid sequences for Constructs 15/16 and Constructs 17/18 are shown in Table-1 above, as well as FIG. 3.

Figure 4:
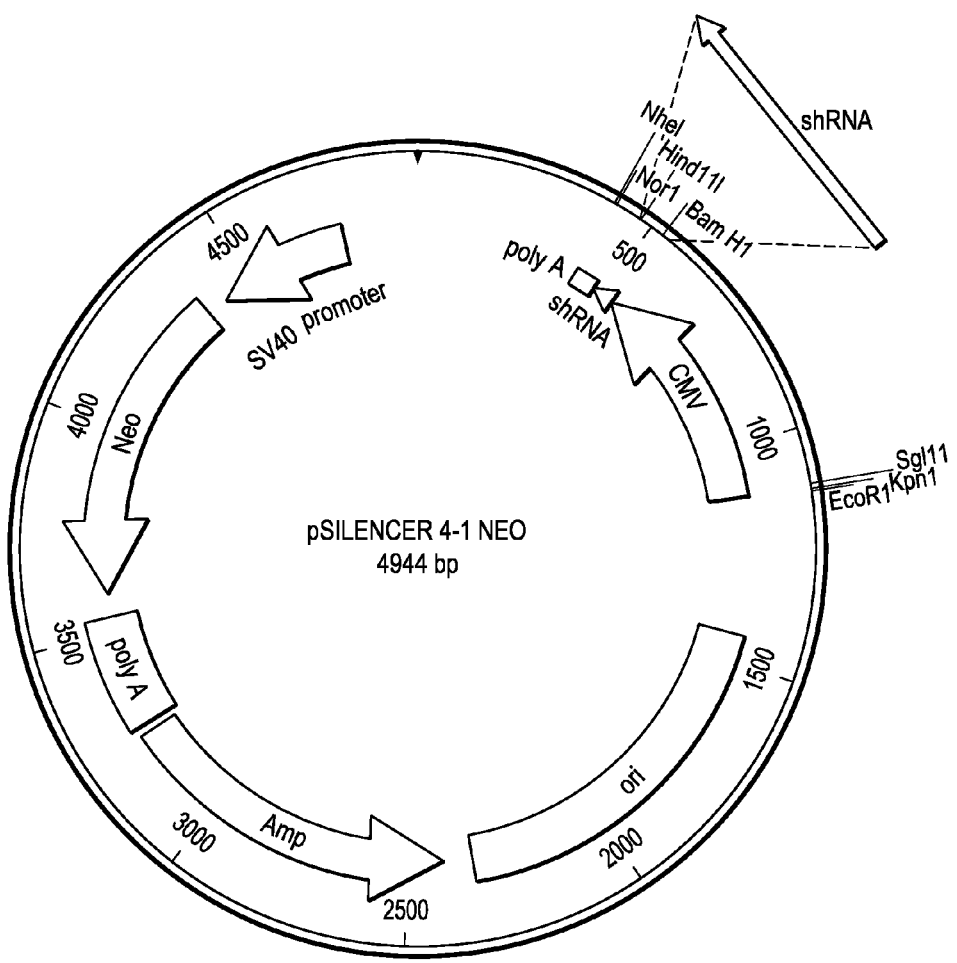
FIG. 4 is a plasmid map of pSilencer 4-1 Neo.

Additional STMN1-specific shRNAs were designed to introduce mismatches and bulges either at the sense strand (passenger strand) or at the anti-sense strand (guiding strand) to determine the structural-functional requirement and efficacy thereof. Introduction of such mismatches was designed to shunt the shRNA to the cleavage-independent RISC.

shRNA expression units were synthesized by fill-in reaction with oligonucleotides containing overlapping sequences as described above. Two oligonucleotides of 60 and 63 bases with 15-base pair complementarity to each other were synthesized for each construct. After the fill-in reaction, a 108-base pair fragment was generated for each shRNA. The synthetic shRNA expression units included Bam HI and Hind III sites at the 5' and 3' ends, respectively, to facilitate the insertion into pSilencer 4.1-CMV Neo expression vector (Ambion) (Austin, Tex.) as shown in FIG. 4. The expression constructs were sequence confirmed before use in RNAi analysis.

Reporter-cDNA transcription fusion constructs. Introduction of siRNA or shRNA into mammalian cells rely on efficient transfection or delivery system. The transfection efficiency varies widely from cell line to cell line. Thus, it is often difficult to obtain an effective and accurate assessment of target gene knock-downs for each siRNA or shRNA by examine the whole cell extract. Additionally, it is often difficult to assess the Target gene knock-down for prolonged periods of time, because transfected cell population diminishes as time goes on. Therefore, a reporter assay system was used, which revealed the efficacy of each siRNA and shRNA construct herein, without any bias introduced by the transfection efficiency.

The reporter-cDNA transcription fusion system (psiTEST) of Invitrogen (San Diego, Calif.) was used. The psiTEST system employed a soluble form of alkaline phosphatase (sAP) as the reporter gene. sAP activity can be easily sampled and assayed from culture media. Target cDNA sequence was inserted behind the transcriptional unit of the sAP gene to form a transcription fusion. Application of siRNA or shRNA that was specific to the target gene sequence will result in degradation of the sAP-cDNA fusion transcripts, leading to the reduction in sAP activity in the media. Efficiency of target gene silencing for each siRNA or shRNA was assessed and compared through the reduction in sAP activity in the media.

Figure 5:
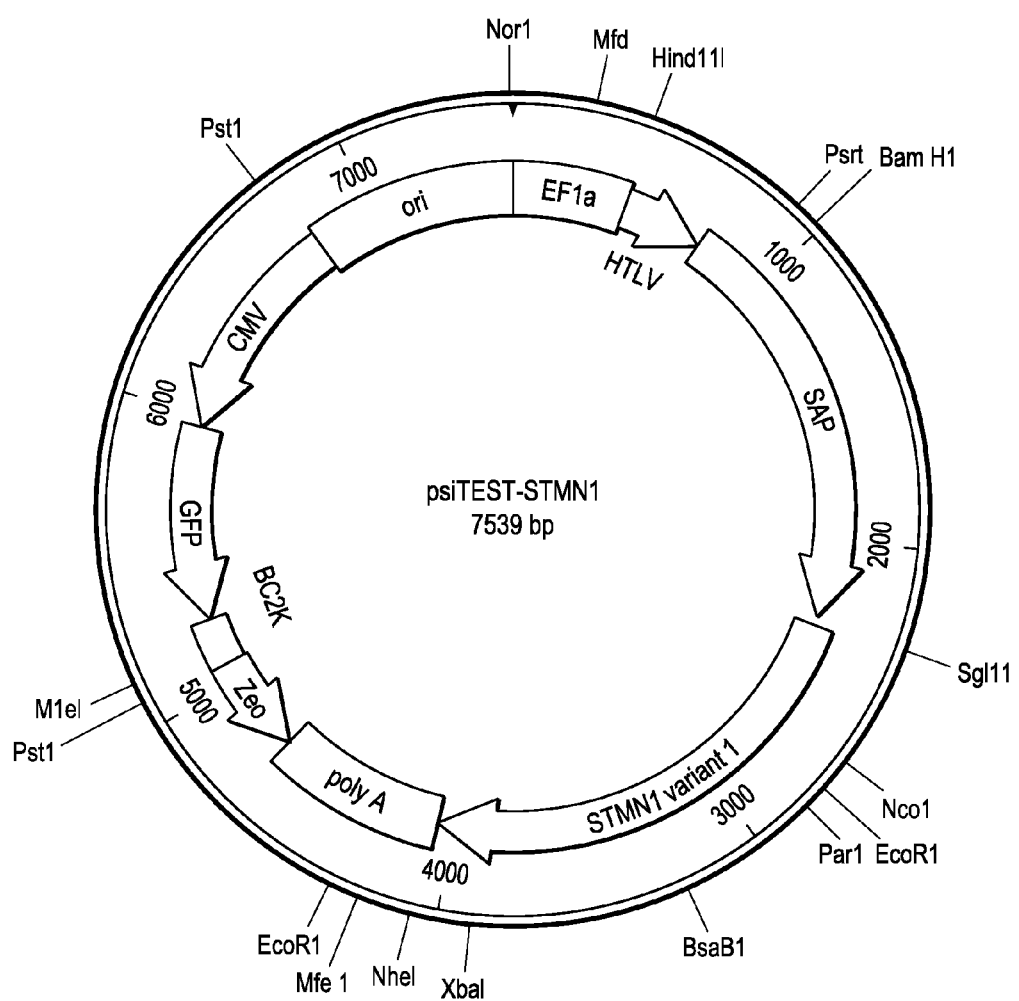
FIG. 5 is a plasmid map of psiTEST-STMN1.

STMN1 cDNA were synthesized by RT-PCR with gene-specific primers as described above. STMN1 cDNA was inserted into the psiTEST vector down stream from the mRNA sequence for the sAP gene to form a transcriptional fusion construct. The resulting fusion construct is illustrated in FIG. 5. It was envisaged that sequence-specific silencing (expression level reduction) of STMN1 would result in a reduction in the amount of transcripts of reporter gene-fusion expression, thereby leading to curtailment of sAP expression. Fusion construct with STMN1 cDNA was sequenced and confirmed for the inserted cDNA sequence, as described above.

Reporter-cDNA transcription fusion assay. The reliability of the reporter-cDNA transcription fusion system was determined. Specifically, HEK-293 cells were co-transfected with psiTEST/STMN1 and various shRNA constructs. The shRNA expression vector to psiTEST/STMN1 expression vector was co-transfected at a 3:1 ratio. For each transfection, triplicate samples were collected at 18 hours and 24 hours post-transfection, and assayed for alkaline phosphatase (AP) activity in the medium. AP assay was performed with colorimetric substrate for AP vis-á-vis OD620 reading.

Figure 6:
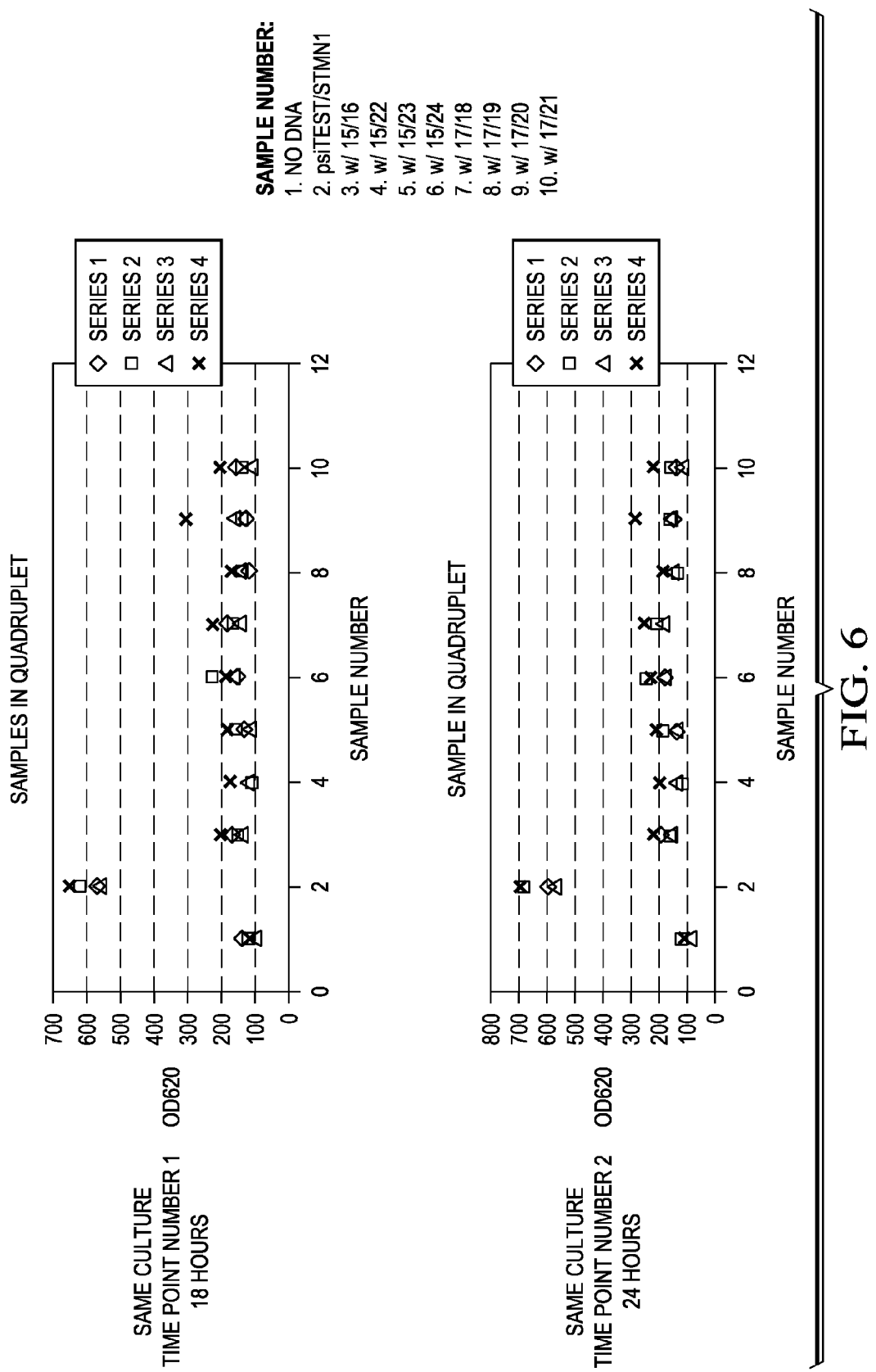
FIG. 6 is a set of graphs showing the reproducibility of the reporter-cDNA transcription fusion assay employed in the Examples below.
Figure 7:
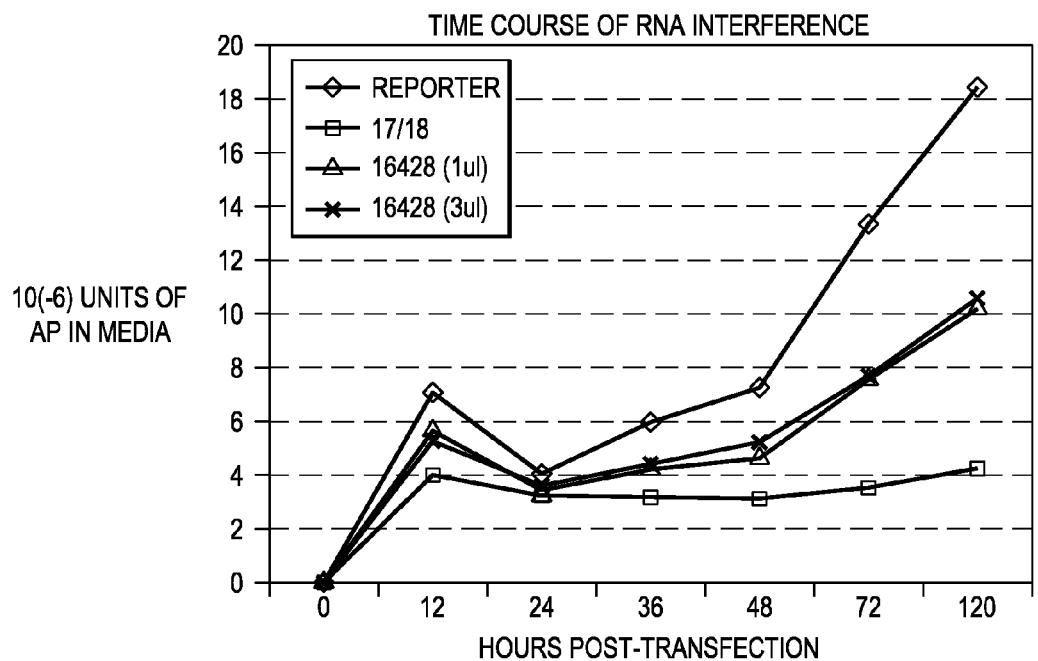
FIG. 7 is a graph showing the results of a comparison between the ability of siRNA and shRNA to reduce the expression level of a target gene.

As shown in FIG. 6, the assay process was very consistent. With triplicate samples, the assay showed little variation between the triplicates. Both 18-hour and 24-hour samples showed consistent patterns, with 24-hour samples requiring much shorter color development time than the 18-hour samples, indicating increased accumulation of AP activity in the media. When compared to psiTEST/STMN1 transfection alone (FIG. 6, sample #2), all shRNA co-transfection effectively reduced the sAP activity in the media (FIG. 6, samples #3-10). Mock transfection without any plasmid DNA showed very little background sAP activity contributing from cell or serum (FIG. 6, sample #1).

shRNA gene silencing persists while siRNA silencing looses its effect over time. The ability of the siRNAs and shRNAs to knock-down (i.e., silence or reduce the expression level of) target gene expression was compared over a course of approximately 5 days. HEK-293 cells were reverse-transfected with reporter construct plus non-specific DNA, or reporter construct plus shRNA expression constructs (namely, constructs 17/18, 17/19, 17/20, or 17/21), or reporter construct plus siRNA (16428). A 3:1 molar ratio of shRNA to reporter gene construct was employed. Identical amounts of shRNAs and reporter constructs were used for each individual transfection. For siRNA transfections, two doses of siRNA were applied with identical amounts of reporter construct as for the shRNA transfections. At 12 hours post-transfection, aliquots of samples were collected, and the culture media was replaced with fresh media to remove any residue siRNA or shRNA in the media. The culture media was sampled at a regular interval for up to 5 days (the media was not changed). In order to compare sAP activity for each time point, the sAP assay was compared to a standard curve generated by known units of AP. FIG. 7 shows that psiTEST/STMN1-alone transfected cells continue to accumulate sAP activity in the culture media (blue line), while shRNA co-transfected cultures have reduced sAP expression that persists up to 5 days (pink line). The 24-hour time point has a reduced sAP activity as the result of the washing step at the 12-hour time point.

When psiTEST/STMN1 were co-transfected with either 10 nM or 30 nM of 16428 siRNA (16428 is a STMN1 specific siRNA targeted at the same sequence as all shRNA constructs), the sAP activity accumulates in a similar pattern as psiTEST/STMN1 transfection alone, albeit lower in sAP accumulation (FIG. 7, light blue and yellow lines). Thus, siRNA appears to be either less active or looses its effect over time. Western Blot showed that 10 nM of 16428 siRNA was the effective dose to silence STMN1 expression (data not shown), whereas 3-fold excess of siRNA at 30 nM concentration seemed to achieve a similar inhibition pattern as for 10 nM. At the greater than saturation concentration of siRNA (10 nM and 30 nM), the reporter expression appeared to be inhibited initially, but the inhibition did not persist as it did with the shRNAs.

The fact that shRNA was able to inhibit sAP expression over a 5-day period indicates that once transfected, shRNA was able to continuously reduce the expression level of its target gene. Comparable siRNA is either not as effective, or looses its activity over time. These data show the considerable advantage, and prolonged activity, of the shRNAs described herein over conventional siRNAs.

Figure 8:
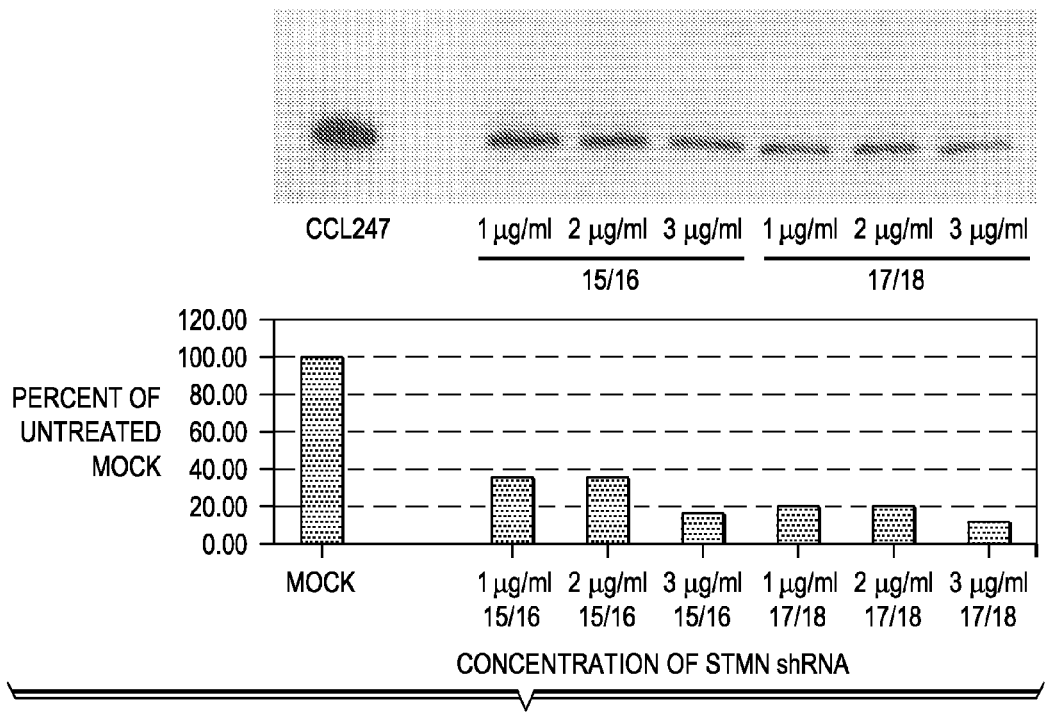
FIG. 8 is an image of a Western Blot, and related bar graph, which show the results of a comparison between the ability of constructs 15/16 and 17/18 to reduce the expression level of Stathmin-1.

Construct 17/18 phasing is more effective than Construct 15/16. To determine the positional effect of the guiding strand on the stem-loop structure, construct 15/16 was compared to construct 17/18. The gene silencing efficiency of construct 17/18 was compared to that of construct 15/16 by Western immunoblotting with STMN1 specific monoclonal antibody. CCL247 is a colon cancer cell line with STMN1 over-expression. CCL247 cells were transfected with 1, 2 or 3 µg/ml of either construct 15/16 or construct 17/18. Total cellular proteins were harvested from transfected cells at 48 hours post-transfection and equal amounts of protein were loaded onto polyacrylamide gel for Western blot analysis with monoclonal antibody specific to STMN1 protein as described above. FIG. 8 shows that both construct 15/16 and construct 17/18 were able to reduce the expression level of STMN1 protein when compared with protein isolated from mock transfected cells. Construct 17/18 appeared to achieve more effective target gene silencing than construct 15/16 at lower doses (1 and 2 µg/ml).

Figure 9:
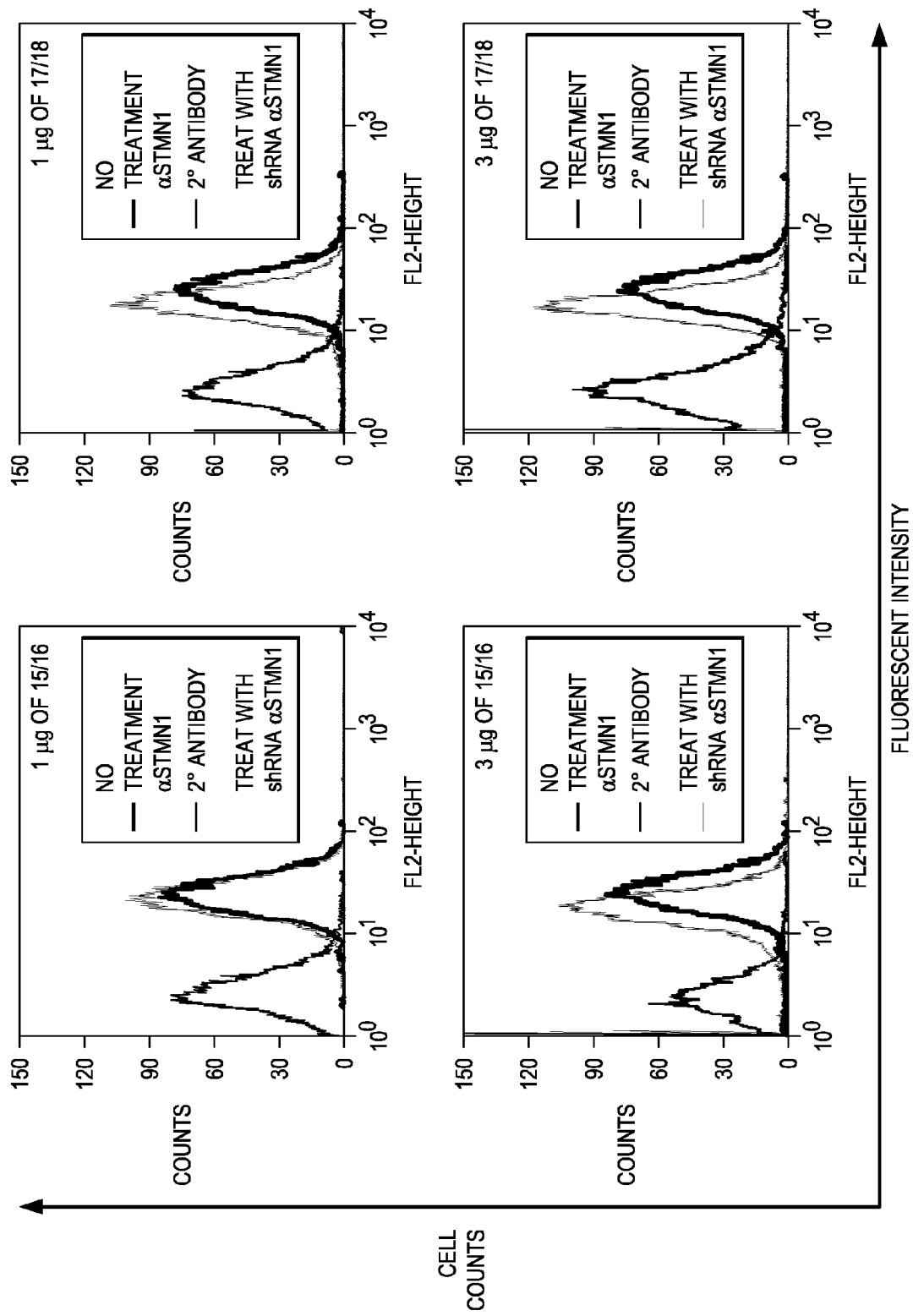
FIG. 9 is a set of flow cytometry results, which compare the ability of constructs 15/16 and 17/18 to reduce the expression level of Stathmin-1.

Flow cytometry was also used to evaluate the population of transfected cells at a single cell level. At 24 hours post-transfection, both transfected cell populations that were transfected with 3 µg/ml of either construct 15/16 or construct 17/18 were shown to exhibit effectively reduced expression of STMN1 when compared to media alone (FIG. 9, lower panels; cell population shift to lower intensity). However, when 1 µg/ml were used for either construct 15/16 or construct 17/18, construct 15/16 was not as effective as construct 17/18 at 1 µg/ml concentration (FIG. 9, upper panels: cell population shift for construct 17/18, but not for construct 15/16). This analysis at the single cell level agreed with the Western immunoblotting results discussed above.

Thus, positioning of the guiding strand sequence at either side of the stem of the stem-loop structure was able to provide active shRNA molecules; however, positioning the guiding strand at the descending strand of the stem-loop structure (construct 17/18) appears to be much more effective than at the ascending strand (construct 15/16). This empirical observation that positioning the guiding strand at the descending strand of the stem-loop structure provides a favorable advantage in effective dose and suggests that the structure is favored for shRNA processing and activity.

Enhanced gene silencing with combinatorial shRNA designs indicates advantageous formulation for RNAi. The advantage in efficacy of the novel Bifunctional shRNAs of the present invention was further demonstrated by co-transfection with combinatorial shRNA constructs. It should be understood that the Bifunctional shRNAs described herein may comprise two or more RNA molecules, which include at least a first molecule designed to enter the cleavage-dependent RISC pathway and at least a second molecule designed to enter the cleavage-independent RISC pathway, whereby such RNA molecules may be designed to be expressed within separate, or the same, preliminary transcripts.

Figure 10:
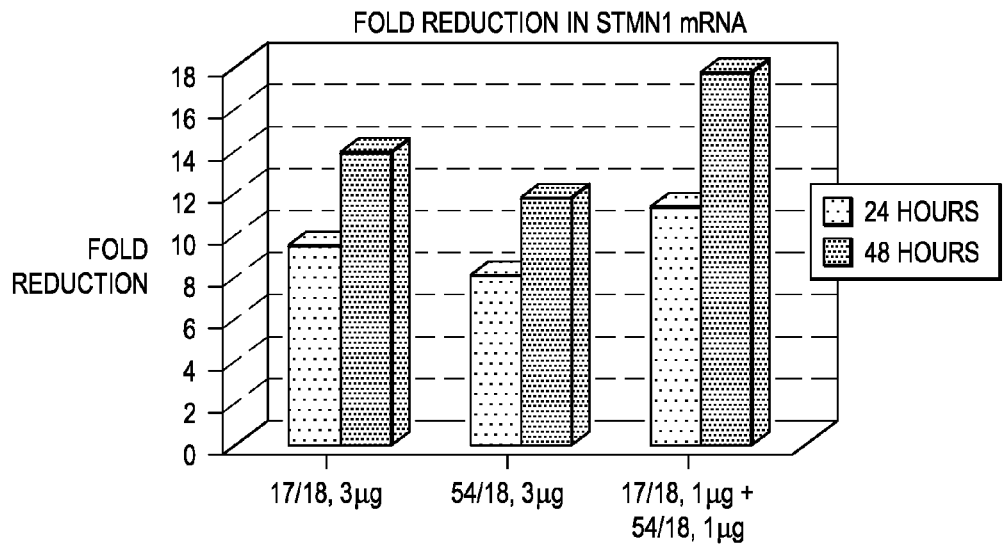
FIG. 10 is a bar graph that summarizes the results of an analysis of various shRNA constructs described in the Examples below, which were designed to reduce the expression level of Stathmin-1.

The target gene silencing efficiency was examined with constructs 17/18 or construct 54/18 (17/18 with single mismatch) alone or in combination. CCL247 cells were either transfected with 3 µg each of construct 17/18 or construct 54/18 alone or in combination (1 µg of each construct). At 24 and 48 hours post-transfection, STMN1 mRNA knock-down was examined by qRT-PCR. qRT-PCR data were transformed and expressed as fold in reduction of STMN1 mRNA compared to the mock transfected cells, and the data are shown in FIG. 10. As shown therein, with a combination of 1 µg of construct 17/18 and construct 54/18, the treatment resulted in more effective reduction in STMN1 mRNA than either 3 µg of construct 17/18 or 3 µg of construct 54/18 alone (both at 24 and 48 hours post-treatment). In terms of promoting STMN1-specific mRNA degradation, the combination of 17/18 and 54/18 is was shown to be an advantageous formulation. Such data further demonstrate the effectiveness of the Bifunctional shRNA designs described herein to effectively reduce target gene expression level.

Advantageous knock-down formulation resulted in advantageous functional outcome. The advantage of the Bifunctional shRNA formulation was further demonstrated at the protein expression and functional level. CCL247 cells were transfected either individually with 1 µg/ml of construct 17/18, construct 15/16, construct 54/18, or construct 17/18 in combination with construct 15/16, construct 17/19, construct 17/20, or construct 54/18. Transfected cells were harvested at 24 and 48 hours post-treatment. Harvested cells were then analyzed by flow-cytometry for STMN1 positive cell population and apoptotic cell population (via Annexin V binding method).

Figure 11:
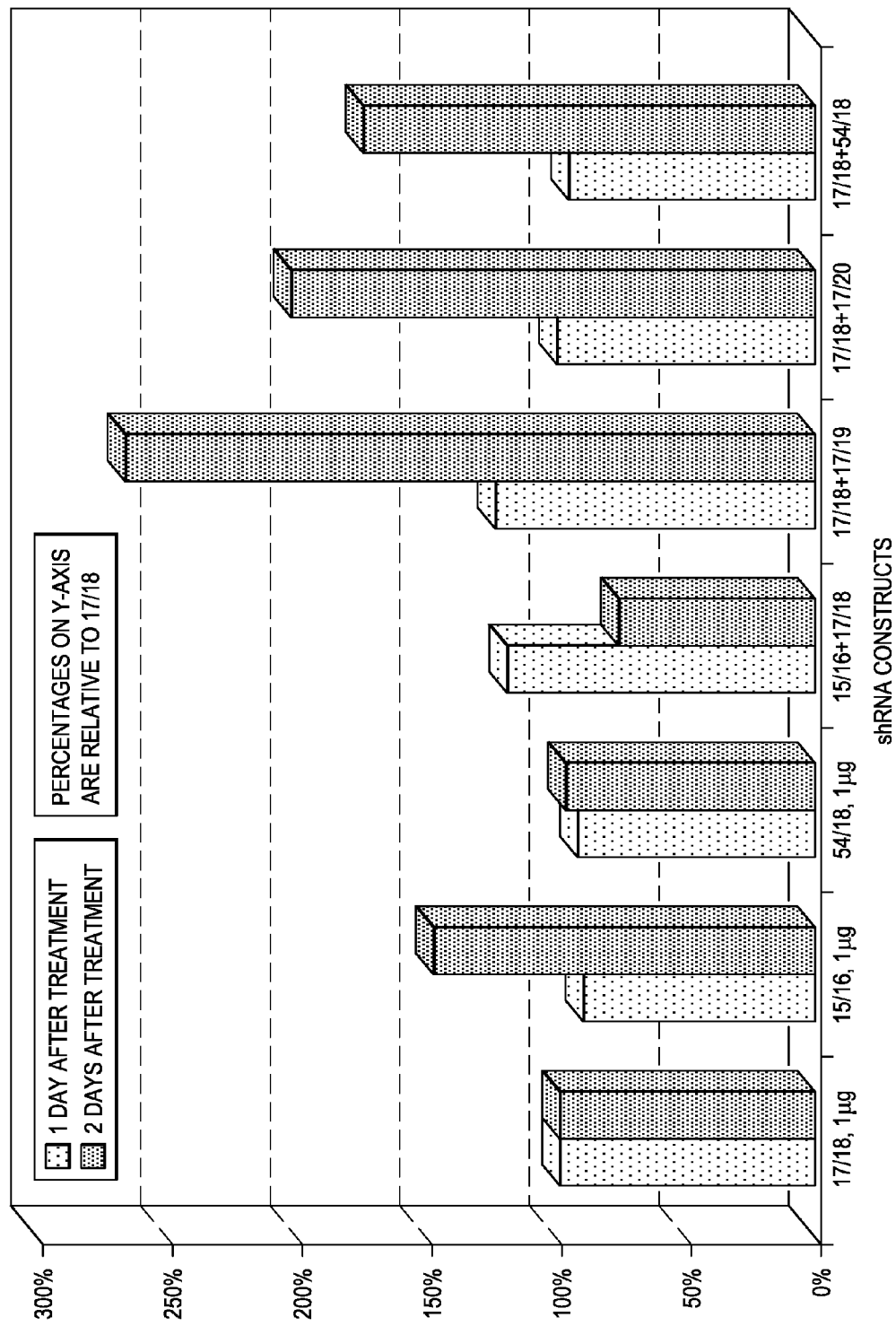
FIG. 11 is a bar graph that summarizes the comparative gene silencing activity of various shRNA constructs described in the Examples below.

The comparative data are shown in FIGS. 11 and 12. For illustrative purposes, each treatment was compared to the construct 17/18 to arrive at a comparative efficiency of gene silencing activity (knock-down efficiency) to construct 17/18. Construct 17/18 was set at 100%. Thus, activity above 100% was deemed a more effective formulation than construct 17/18. FIG. 11 shows the comparative knock-down efficiency of each construct and the combinatorial Bifunctional shRNA formulations examined by the STMN1 positive cell population. FIG. 12 shows the comparative knock-down efficiency of each construct and the combinatorial Bifunctional shRNA formulation examined by the apoptotic cell population.

Constructs 17/18 and 15/16 (perfect matching strands, but opposite in phasing) was found to be comparatively less efficacious compared to each individual formulation, both at 24 and 48 hours post-treatment. However, combination of construct 17/18 with either construct 17/19, or construct 17/20 or construct 54/18 (construct 17/18 comprised mismatches at either the guiding strand or the passenger strand) showed comparative enhancement in efficacy that was significantly more prominent at 48 hours post-treatment. A similar and consistent pattern of comparative efficacy emerged with both analysis methods for STMN1 positive cell population (FIG. 11) and for apoptotic cell population (FIG. 12).

Interestingly, construct 15/16 and construct 17/18 was shown to be less effective than each construct alone. A potential explanation is that both constructs may enter into the same RNAi pathway. That is, because they are mirror images to each other, they may have effectively silenced each other rather than the endogenous STMN1 mRNA, thereby reducing the efficiency of the combinatorial formulation. On the other hand, construct 17/18-related constructs, such as constructs 17/19, 18/20 and 54/18, were all in the same orientation and phasing as 17/18. Thus, these constructs can effectively complement and enhance the RNA interference function by utilizing additional RNAi pathways.

Example 2

Expression of Bifunctional shRNAs in Single Preliminary Transcripts

Materials and Methods

Cell lines. HCT-116 (ATCC# CCL-247) human colorectal carcinoma cell line and human breast cancer cell line MDA-MB-231 (ATCC# HTB-26) were obtained from ATCC (Manassas, Va.). Cells were cultured under the conditions recommended by ATCC. Early passage cells were used for experiments.

Construction of STMN1 bi-functional shRNA. The STMN1 Bifunctional shRNA consisted of two shRNA stem-loop structures with the full complementary (17/18) sequence in front of the partially complementary sequence (54/18), which contained interspersed mismatched base pairs with the STMN1 mRNA transcript. The sequences for 17/18 and 54/18 are shown in FIG. 13. To join the two shRNA expression units, the Hind III site at the 5' end of the 54/18 expression unit was changed into a Bgl II site and the Bam HI site at the 3' end of the 17/18 expression unit was then joined to the 5' end of 54/18 expression unit via the Bgl II site to establish the Bifunctional shRNA expression unit. The 17/18 and 54/18 sequences are represented by SEQ ID NO: 34 and SEQ ID NO: 35, respectively. The design of constructs 17/18 and 54/18 are illustrated in FIG. 13.

Briefly, the single 17/18 or 54/18 shRNA DNA fragments were generated by PCR. The pSilencer vectors containing single shRNA expression units were used as the templates for PCR. PCR was accomplished by using R seq and F seq primers or R seq and Bgl II short primers (as set forth in Table-2 below) with high-fidelity DNA SuperTaq Polymerase (Ambion). The PCR fragments were gel purified (Quick Gel Purification kit, Qiagen) and digested by BamHI or Bgl II. The digested fragments were gel purified, and ligated by T4 DNA ligase (New England Biolabs) to join the two shRNA expression units. The ligated mixture was fractioned in 2% agarose electrophosis and the correct-size ligated Bifunctional shRNA-containing fragments (about 416 base pairs) were removed from the gel and purified. To obtain sufficient Bifunctional shRNA-encoding DNA for cloning into the pSilencer vector, the Bifunctional shRNA-containing PCR fragments were further PCR amplified with R seq and F seq primers (Table-2 below), gel purified and co-digested with BamHI and HindIII (New England Biolabs), and then gel purified by removing the desired inserts (about 216 base pairs). The BamHI/HindIII restricted inserts were ligated with BamHI/HindIII restricted pSilencer 4.1-CM neo plasmid (Ambion) using a Quick Ligation kit (New England Biolabs). The ligated DNA was transformed into One Shot MAX Efficiency DH5α-T1 Competent cells, and the potential clones were picked and mini-prepped to obtain plasmid DNA, which was subject to PCR verification using the F seq and R seq primers (Table-2).

TABLE 2

| | | |
|---|---|---|
| BgI II short | TGAGATCTCCGAGGCAGTAGGCA | (SEQ ID NO: 36) |
| F seq | AGGCGATTAAGTTGGGTA | (SEQ ID NO: 37) |
| R seq | CGGTAGGCGTGTACGGTG | (SEQ ID NO: 38) |

Sequence confirmation and vector production. Six clones with the correct insert size as determined by PCR were subject to sequence verification by SeqWright, (www.seqwright-.com; Houston, Tex.). All clones showed the correct sequence, as set forth in SEQ ID NO: 39 and illustrated in FIG. 13. Vector DNA was purified from E. coli using an EndoFree Plasmid Maxi kit (Qiagen). Purified plasmid DNA was resuspended in water and quantified with a Nanodrop ND-100 spectrophotometer (Nanoprop, Wilmington, Del.). Large scale productions of GLP-grade plasmid DNA were produced by Aldevron (www.aldevron.com).

Transfection of cell lines with siRNA or shRNA. Reverse-transfection of cell lines was performed using siPort™ NeoFX™ (Ambion) for siRNA and siPort™ Amine™ (Ambion) for shRNA by following the protocols recommended by the manufacturer. Briefly, one hour before transfection, healthy growing adherent cells were trypsinized and re-suspended in normal growth medium at $1 \times 10^5$ cells/ml. siPORT NeoFX (or Amine) (5 µl/well) was diluted into a predetermined volume of Opti-MEM 1 medium (100 µl/well) for each 6-well plate used and incubated for 10 minutes at room temperature. siRNA (plasmid DNA) was diluted into Opti-MEM 1 medium for a final concentration of 10-30 nM (1-3 µg/ml for shRNA), as required, in 100 µl/well volume of OptiMEM1. The diluted siPORT NeoFX (or Amine) and the diluted RNA (or plasmid DNA) were combined and incubated for 10 minutes at room temperature. The transfection complexes were then dispensed into empty 6-well plates (200 µl/well). The trypsinized cells were gently mixed and 2.3 ml of the $1 \times 10^5$ cells/ml were overlayed into each well of the 6-well plates, which were gently rocked back and forth to evenly distribute the complexes. The final volume of transfection was 2.5 ml/well. Incubation was performed at 37° C., while checking after 8 hours for any cytotoxicity. If cytotoxicity was observed, the media was replaced with fresh media. Fresh media was replaced after 24 hours. The cells were assayed at 24 hours, 48 hours and 4 days post-transfection for target gene silencing (protein knock-down) by Western Blot, flow-cytometry or RT-PCR. Transfections were also performed with Transfectamine 2000 (Invitrogen) with the protocol recommended by the manufacturer.

Western Immunoblotting. Cells were lysed with CellLytic-M lysis buffer and removed from the surface of the culture dish, incubated at room temperature for 30 minutes on a slow shaker, and briefly centrifuged. A small aliquot for protein concentration estimation by Coomassie Bradford Plus Assay was taken with BSA as standard. The SoftMaxPro software was used to calculate the protein concentration values and to plot a standard curve. Equal amounts of protein were separated on a pre-assembled gel (usually 5-20 µg) 15% PAGE using a Mini-Protein II Cell system (Bio-Rad). Following electrophoresis, the separated proteins were electro-transferred onto a PVDF membrane under standard conditions. The membranes were subsequently blocked with blocking buffer containing 5% non-fat dried milk in DPBS-T overnight at 4° C. After two changes of wash buffer, proteins were tagged primary antibody and then HRP-conjugated secondary antibody. Chemiluminescent detection was performed using ECL Plus Western Blotting Detection reagents with a G:BOX Chemi XT16 automated chemiluminescence image analyzer (Syngene, Frederick, Md.). Membranes were stripped and re-probed with a different antibody to detect the β-Actin house keeping protein.

Apoptosis Assays. Apoptosis assay with Caspase 3 was performed using an APO ACTIVE 3™ Antibody Specific Active Caspase 3 Detection Kit (Cell Technology, Mountain View, Calif.). Following the Transfection of cells with siRNA or shRNA, at the designated time, the cell supernatants and cells were collected, fixed and permeabilized with Fix and Perm buffer (BD biosciences) for 10 minutes. A portion of cells were removed for the unstained control. 10 µl of 1× rabbit anti-Caspase 3 was added to $1 \times 10^6$ cells in 100 µl of Perm wash buffer and incubated for 30 minutes at room temperature. Samples were washed twice with Perm wash buffer. After the final wash, 10 µl of 1×FITC-labeled Goat anti-rabbit antibody was added and incubated for 30 minutes in the dark at room temperature. After incubation with antibodies, samples were washed and re-suspend in PBS+2% BSA to close the pores and stored at 4° C. until analysis, which was carried out using a FACS Caliber Flowcytometer (BD Biosciences). 5 µl of 20 mg/ml of Propedium Iodide was added to samples just before the analysis for dead cells. Data were analyzed using CellQuest Pro software.

Apoptosis assay with Annexin V was performed with AnnexinV FITC (BD Biosciences). Cells were collected both from the culture supernatant and from the trypsin-suspended cells. Total cells were wash twice with cold PBS before stained for apoptosis and cell kill. Washed cells were suspended in 1× binding buffer at approximately $1 \times 10^5$ cells in 100 µl, 5 µl of FITC-Annexin V and 5 µl of Propidium Iodide were added, gently vortexed, and incubated at room temperature for 15 minutes in the dark. Following incubation, 400 µl of 1× binding buffer was added and samples were analyzed by flow cytometry using FACS Caliber and CellQuest Pro software.

Viable Cell Count by Trypan Blue Dye Exclusion. Sample cells were diluted 1:10 with DPBS and added with 50 µl of trypan blue (Trypan Blue 0.4%, Gibco BRL). Viable cells were counted with a hemacytometer.

Viable Cell Count by automated EasyCount System. The cell numbers of transfected and untransfected control were determined using an EasyCount™ System (Immunicon, Huntingdon Valley, Pa.). The EasyCount™ System, together with the EasyCount™ ViaSure™ Kit, provides automated counting of live and dead nucleated cells. Briefly, the tissue culture cells were trypsinized to prepare cell suspensions in growth medium. 25 µl of cell suspensions and 25 µl of fluorescent staining reagent were gently mixed. 10 µl of the mixture were loaded onto the EasyCount slide and the total cells and the viable cells were measured using an EasyCount device.

Results

Figure 14:
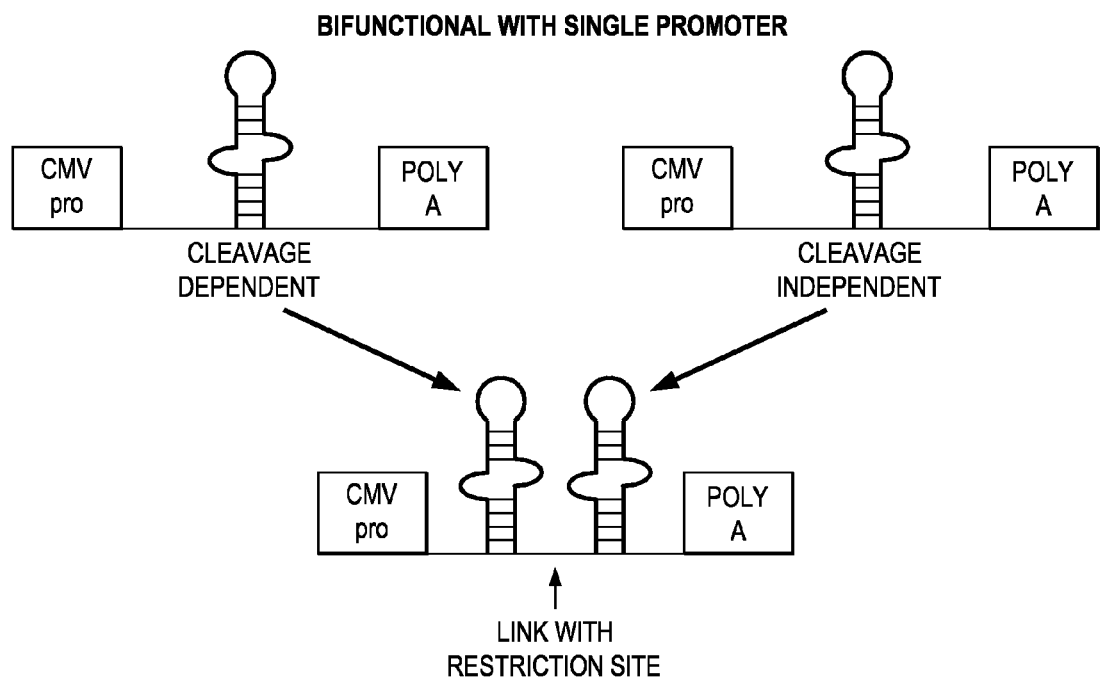
FIG. 14 is a diagram illustrating the design of STMN1 Bifunctional shRNA being expressed within a single preliminary transcript.

Construction of Bifunctional shRNA. In Example 1 above, the efficacy of each of the shRNA expression units (cleavage-dependent and cleavage-independent) was assessed individually and the potential advantage of the Bifunctional shRNA was demonstrated by co-transfecting both the individual "cleavage-dependent" and "cleavage-independent" constructs in a cell system. In this Example 2, the Bifunctional shRNAs were constructed by placing the "cleavage-dependent" and "cleavage-independent" shRNA expression units together on a single expression vector behind the CMV promoter (FIG. 14). Construction of the Bifunctional shRNA expression vectors was performed as described above. Positive clones with correct insert size were first identified by PCR and further confirmed by sequence analysis.

Bifunctional shRNA effectively reduced the expansion of colon cancer cells (CCL247) in culture. First, the capability of Bifunctional shRNA to inhibit cancer cell growth was analyzed. CCL-247 colon cancer cells were transfected with 1 µg/ml of precursor DNA, which encoded Bifunctional shRNA designed to inhibit the translation of mRNA transcripts encoded by STMN1, with siPort™ Amine as described above. Equal numbers of cells ($5 \times 10^4$ cells) were delivered to each well of a 24-well plate for transfection. At 24, 48 and 72 hours post-transfection, cells were harvested and viable cells were counted by vi-cell counter. The results are summarized in FIG. 15. Bifunctional shRNA (FIG. 15, pink line) was shown to effectively reduce the expansion of colon cancer cells in culture when compared with scrambled DNA transfected cells (FIG. 15, blue line). Depending on the transfection efficiency of each experiment, 50-80% reduction in growth of colon cancer cells was routinely observed by treating cells with the STMN1 Bifunctional shRNA.

Compared with conventional shRNA, Bifunctional shRNA is more effective in keeping cancer cells at low expansion rate. Bifunctional shRNA was next compared to conventional shRNA (cleavage-dependent) and the cleavage-independent shRNA constructs. Equal numbers of cells were transfected with equal amounts of plasmid DNA for each construct (1 µg/ml). At 24 and 48 hours post-transfection, viable cells were counted for each sample and the cell expansion index was calculated. The cell expansion index within a 24 hour span was calculated by dividing the average number of viable cells to the average number of viable cells at the previous day. For example, the Cell expansion index equaled [the average number of viable cells at 24 hours post-transfection] divided by [the initial number of cells seeded]. The cell expansion index provided a good assessment of the inhibition of cell expansion as the result of the introduction of STMN1 shRNA.

The comparative cell expansion index results are shown in FIG. 16. The cell expansion index of the negative control transfected samples was used as the reference point (FIG. 16, blue dot at 24 hours time point=100%). All cell expansion indexes were normalized to the reference point and expressed as a percentage of the reference point. Thus, below 100% means that the sample had a lower cell expansion index than the reference point, while above 100% means that the sample had a higher cell expansion index relative to the reference point.

Both cleavage-dependent and cleavage-independent shRNA showed increased cell expansion indices (i.e., greater than 100%) at both 24 and 48 hours post-transfection. Importantly, however, the Bifunctional shRNA construct was able to maintain, both absolutely and comparatively, a low cell expansion index (i.e., less than 100%) both at 24 and 48 hours post-transfection. This phenomenon was shown to be reproducible. At 72 hours post-transfection, all cultures reached confluency and, therefore, reduced their cell growth index dramatically making it difficult to determine whether the Bifunctional shRNA could extend its effect beyond 48 hours post-transfection.

The interpretation of these data is that the Bifunctional shRNA was significantly more effective in sustaining the suppression of target gene (STMN1) expression than either the conventional cleavage-dependent or the cleavage-independent shRNAs alone. That is, the Bifunctional construct was more effective in holding cells at $G_2$/M phase block, thus resulting in a low cell expansion index, compared to the conventional cleavage-dependent or the cleavage-independent shRNAs alone, which allowed a proportion of the cells to escape from the $G_2$/M block and continue to divide. The Bifunctional shRNAs, which simultaneously involved both cleavage-dependent and cleavage-independent pathways, was significantly more effective in sustaining a reduced target gene expression level than either of the singlet shRNAs that are targeted at only one of the two RISC pathways.

Bifunctional shRNA is more effective in inducing apoptosis of colon cancer cells. To further confirm the above observations on the comparative advantage of the Bifunctional shRNA construct to reduce the cell expansion index, effector efficacy on transfected cell entry into apoptotic pathways was further analyzed. Previously, it was observed that treating the colon cancer cells with STMN1 specific shRNAs induced approximately 10% to 20% of cell death at day 1 post-transfection, with limited cell entry into apoptosis (as shown by the Caspase 3 assay described herein). Interestingly, on day 2 post-treatment, there were very few dead cells, while the apoptotic cells increased dramatically. Since the reduction in STMN1 gene expression leads to cell cycle arrest at $G_2$/M phase, it was postulated that the population of cells that had already entered into M phase or in transit to M phase were the most vulnerable to STMN1 gene silencing, i.e., those likely being the dead cell population on day 1 of treatment.

Cell populations that were in other phases of the cell cycle during the initial transfection were not affected—and would not be until the cell entered the $G_2$ phase in transition to mitosis. STMN1 gene silencing was presumed to hold cells at the $G_2$/M phase and cells not able to escape from the cell cycle block predominantly entered apoptosis, thus explaining why more apoptotic cells at day 2 post-transfection was observed. As discussed above, it was further shown that Bifunctional shRNA was more effective in keeping the cell population in low cell expansion rate, which indicated that the Bifunctional shRNA was more effective in sustaining STMN1 gene silencing and preventing cells from escaping from the cell cycle block. As such, it would be expected to observe a higher number (or percentage) of apoptotic cells at 48 hours post-treatment with the Bifunctional shRNA than the conventional shRNA constructs.

Figure 17:
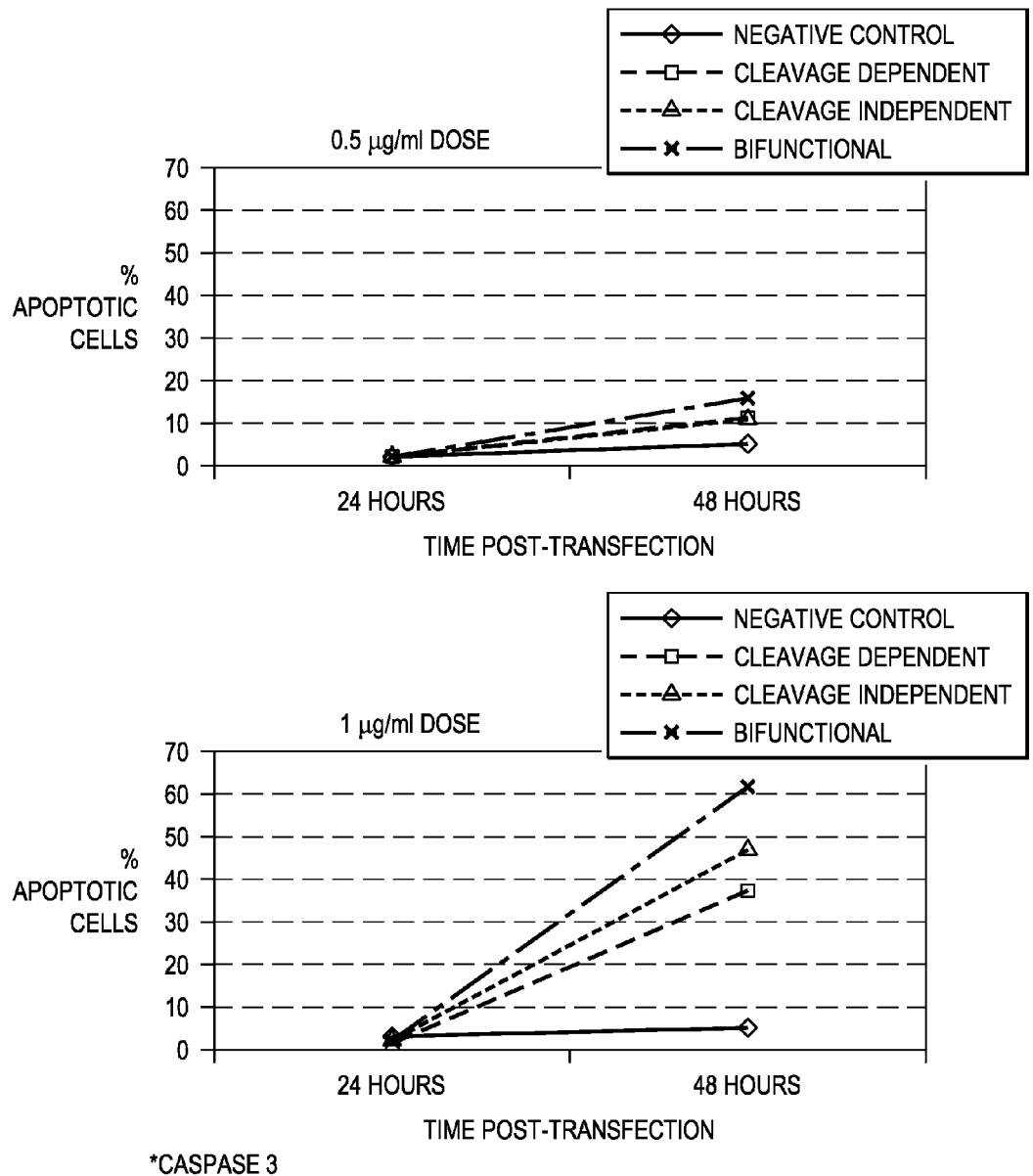
FIG. 17 includes two line graphs that compare the ability of STMN1 Bifunctional shRNA to conventional shRNA to induce apoptosis.

The CCL-247 colon cancer cells were treated with either 0.5 μg/ml or 1.0 μg/ml of shRNAs and the apoptotic cell population was identified by flow cytometry analysis with caspase 3 specific antibody. Bifunctional shRNA was consistently two-fold more effective in generating apoptotic cells than the conventional cleavage-dependent construct and was at least 50% more effective than the cleavage-independent construct. The analysis was repeated several times under slightly different conditions, with the result being consistent each time. FIG. 17 summarizes a representative data set.

Bifunctional shRNA also showed stronger efficacy on certain aggressive forms of breast cancer cells (MDA-MB-231), with higher expression levels of Stathmin-1. The highly tumorogenic breast cancer cell line MDA-MB-231 comprises aggressive triple negative breast cancer cells and is widely used as a model system for pre-clinical analysis of therapeutic effectiveness. MDA-MB-231 cells express higher levels of Stathmin-1, which was confirmed by Western immunoblot. Indeed, with equal amounts of cell extract loaded, MDA-MB-231 cells showed much stronger Stathmin-1 expression in comparison to CCL-247 and CCL-171 cells (FIG. 18). Quantitatively, Stathmin-1 expression for MDA-MB-231 was shown to be approximately six-fold higher than CCL247 and CCL-171 cells when the comparative protein expression level is normalized to β-actin.

Figure 19:
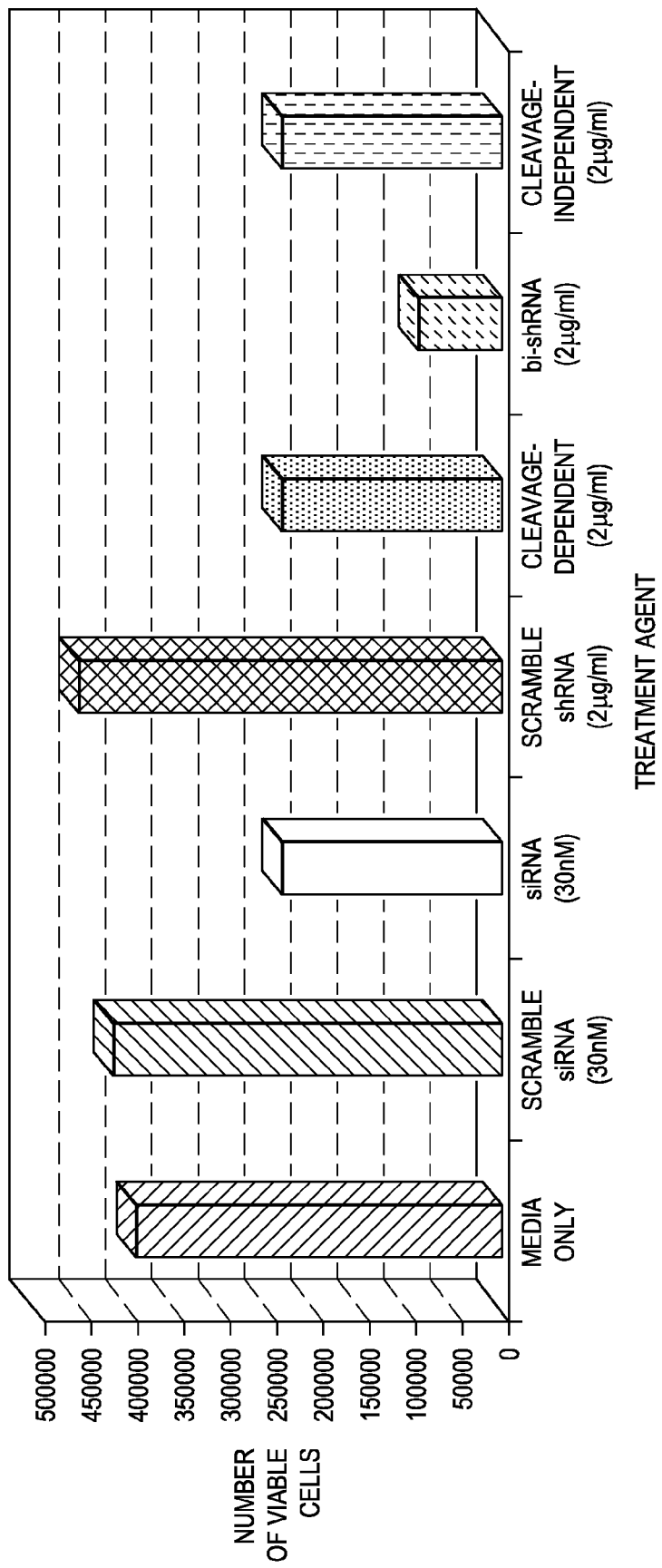
FIG. 19 is a bar graph that compares the ability of STMN1 Bifunctional shRNA to conventional shRNA to induce growth arrest in breast cancer cells.

These high Stathmin-1 expressing breast cancer cells were provided with the Bifunctional shRNAs described herein. Compared with either the cleavage-dependent or cleavage-independent shRNA (or siRNA), the Bifunctional shRNA construct was shown to exhibit much stronger efficacy in inducing cancer cell arrest at 48 hours post-treatment. FIG. 19 shows the comparative results. Equal numbers of cells ($1 \times 10^5$) were either not treated (FIG. 19, medium blue bar), or treated with control siRNA (with scrambled sequence, FIG. 19, purple bar), STMN1 specific siRNA (30 nM, FIG. 19, yellow bar), control shRNA (2 μg/ml, FIG. 19, light blue bar), cleavage-dependent shRNA (2 μg/ml, FIG. 19, purple bar), cleavage-independent shRNA (2 μg/ml, FIG. 19, dark blue bar), or Bifunctional shRNA (2 μg/ml, FIG. 19, pink bar). At 48 hours post-transfection, viable cells were counted. Bifunctional shRNA (FIG. 19, pink bar) was consistently shown to be two- to three-fold more effective in inducing cancer cell growth arrest than either the conventional cleavage-dependent shRNA (FIG. 19, purple bar) or the cleavage-independent shRNA (FIG. 19, dark blue bar). This observation was repeated and confirmed several times.

Construction of Acid Ceramidase shRNAs. Single 85/86 or 87/86 shRNA DNA fragments were generated using Murex0085 and Murex0086 or Murex0087 and Murex0086 primers (as listed in Table 3 below) by PCR with high-fidelity DNA SuperTaq Polymerase (Ambion).

TABLE 3

| DNA Fragment | SEQ ID NO |
|---|---|
| Murex0085 | SEQ ID NO: 41 |
| Murex0086 | SEQ ID NO: 42 |
| Murex0087 | SEQ ID NO: 43 |
| Murex0088 | SEQ ID NO: 44 |
| Murex0089 | SEQ ID NO: 45 |
| BgI_II_long | SEQ ID NO: 46 |
| F seg | SEQ ID NO: 47 |
| R seg | SEQ ID NO: 48 |

1 μl of 1:100 dilution of shRNA 85/86 was amplified using Murex0088 and Bgl II long primers to generate 85/86 Bgl II, whereas shRNA 87/86 amplification was carried out using Murex0088 and Murex0089 primers. PCR fragments of 85/86 Bgl II and 87/86 were verified, separated and gel-purified with 2% agaroase gel, 1×TBE buffer, using a Quick Gel Purification Kit (Qiagen). The purified PCR DNA of 85/86 Bgl II and 87/86 were digested with Bgl II or Bam HI restriction enzymes, respectively, and gel-purified with a MiniElute Gel Purification Kit (Qiagen).

The restriction enzyme cut 85/86 Bgl II was ligated to 87/86 DNA using T4 DNA ligase. The ligated Bifunctional shRNA 85/86 plus 87/86 DNA fragments were co-digested by BamHI and HindIII, gel-purified with a MiniElute Gel Purification Kit (Qiagen), and then ligated using a Quick Ligation Kit (New England Biolabs) into the pSilencer 4.1-CMV neo plasmid (Ambion), which were previously co-digested by BamHI and HindIII. Transformation of the ligated plasmid was carried out with One Shot MAX Efficiency DH5α-T1 Competent cells, and 20 potential clones were picked and mini-prepped to obtain DNA that was subjected to PCR verification using the F seq and R seq primers (Table-3 above). Six clones with expected PCR product size of 408 base pairs were selected and sequenced (for confirmation purposes) by bi-directional DNA sequencing (SeqWright). One of the clones, clone-14, was sequence confirmed. The DNA sequence data were analyzed with the assistance of DNA Start Lasergene and ChromasPro software. The Bifunctional shRNA was confirmed to have the sequence represented by SEQ ID NO: 40.

The Bifunctional shRNA for Acid Ceramidase was shown to be more effective in cancer cell kill than either cleavage-independent or cleavage-dependent constructs within 24 hours. Ceramide is a ubiquitous pro-apoptotic sphingolipid. Acid ceramidase (AC) plays a key role in the catabolic conversion of ceramide into sphingosine-1-phosphate (SIP), a highly effective anti-apoptotic derivative. Many cancer cells have been shown to have high expression of AC. siRNAs targeted to AC have been shown to reduce tumor cell growth both in vitro and in vivo.

The shRNA constructs designed to "knock-down" the expression of AC. shRNAs independently capable of either cleavage-dependent or cleavage-independent inhibition of target expression were constructed, as described above. Additionally, the Bifunctional shRNA (mediating both cleavage-dependent and cleavage-independent processes) was also constructed, as described above. Endo-Free plasmids DNA was purified from E. coli cells as previously described. Three doses of plasmid DNA were used for each construct and tested within CCL-247 colon cancer cells. Transfection was carried out as previously described. Equal numbers of cells were transfected among the test samples.

At 24 hours post-transfection, viable cells from each of the transfected cultures were counted. The results are shown in FIG. 20. As shown therein, both cleavage-dependent (maroon bar) and cleavage-independent (yellow bar) constructs showed efficacy in reducing tumor cell growth. However, the Bifunctional shRNA construct (light blue bar) showed a consistent advantage over either the cleavage-dependent or the cleavage-independent constructs alone. The 2 µg/ml appears to be the most effective dose, while 0.5 and 1.0 µg/ml doses showed comparable results.

As shown in the foregoing Examples, using the Bifunctional shRNAs described herein provides a desirably efficacious RNAi formulation. Such formulations were shown to provide superior efficacy in comparison to other currently-available conventional molecules designed for RNA interference, such as conventional shRNAs or siRNAs.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for reducing the expression level of a target gene, comprising:
providing a cell with a single contiguous bifunctional RNA molecule that comprises:
a first double stranded sequence comprising a guide strand sequence that is fully complementary to a passenger strand and an mRNA transcript encoded by the target gene; and
a second double stranded sequence that is partially complementary to a mismatched passenger strand and complementary to the mRNA transcript encoded by the target gene, wherein the bifunctional RNA molecule activates cleavage-dependent and cleavage-independent RNA-induced silencing complex for reducing the expression level of the target gene.

2. The method of claim 1, wherein the first and second double stranded sequences reside within a stem portion of separate stem loop structures.

3. The method of claim 1, wherein the first guide strand sequence is presented to a cleavage dependent RNA-induced silencing complex and binds to an mRNA transcript encoded by the target gene.

4. The method of claim 3, wherein the binding of the first guide strand sequence to the mRNA transcript causes degradation of the mRNA transcript.

5. The method of claim 3, wherein the second double stranded sequence is presented to a cleavage independent RNA-induced silencing complex and sequesters the mRNA transcript encoded by the target gene.

6. The method of claim 5, wherein sequestering the mRNA transcript encoded by the target gene represses the translation of the mRNA transcript.

7. The method of claim 1, wherein the bifunctional RNA molecule is operably connected to a promoter.

8. The method of claim 7, wherein the promoter is selected from the group consisting of a tumor cell specific promoter, a regulatable promoter, and an inducible promoter.

9. The method of claim 1, wherein the first double stranded sequence and the second double stranded sequence initially reside within a single primary transcript.

10. The method of claim 9, wherein the primary transcript further comprises a third RNA molecule and a fourth RNA molecule which both comprise double stranded sequences within a stem portion of separate stem loop structures.

11. The method of claim 10, wherein the first and second double stranded sequences comprise a guide strand sequence that is complementary to an mRNA transcript encoded by a first target gene, whereas the third and fourth RNA molecules comprise a guide strand sequence that is complementary to an mRNA transcript encoded by a second target gene.

12. The method of claim 2, wherein each stem loop structure comprises about 40 to 100 nucleotides, wherein the stem portion thereof comprises about 19-45 nucleotides and a loop portion thereof comprises about 4-25 nucleotides.

13. The method of claim 12, wherein each stem loop structure comprises about 50 to 75 nucleotides, the stem portion thereof comprises about 20-30 nucleotides, and the loop portion thereof comprises about 6-15 nucleotides.

14. A method for reducing the expression level of a target gene comprising:
providing a cell with a bifunctional. RNA molecule comprising a first and a second portion, wherein:
the first portion comprises a first double stranded sequence comprising a guide strand sequence that is fully complementary to a passenger strand and a portion of an mRNA transcript encoded by the target gene, wherein the guide strand sequence is presented to a cleavage-dependent RNA-induced silencing complex; and
the second portion comprises a second double stranded sequence that is partially complementary to a mismatched passenger strand and to the mRNA transcript encoded by the target gene, wherein the second double stranded sequence is presented to a cleavage-independent RNA-induced silencing complex,
wherein the bifunctional RNA molecule activates both cleavage-dependent and cleavage-independent RNA-induced silencing complex for reducing the expression level of the target gene.

15. The method of claim 14, wherein the second double stranded sequence comprises a second mismatched guide strand sequence that is partially complementary to a passenger strand and the mRNA transcript encoded by the target gene, wherein the second double stranded sequence is capable of sequestering translation of the mRNA transcript encoded by the target gene.

* * * * *

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial
<220> FEATURE:
<223> OTHER INFORMATION: PCR primer sequence

<400> SEQUENCE: 1
tatggcagga aaggatgagg                                               20

<210> SEQ ID NO 2
<211> LENGTH: 29
<212> TYPE: DNA
<213> ORGANISM: Artificial
<220> FEATURE:
<223> OTHER INFORMATION: PCR primer sequence

<400> SEQUENCE: 2
atcagatctt ctgtttggcg cttttgtgc                                     29

<210> SEQ ID NO 3
<211> LENGTH: 31
<212> TYPE: DNA
<213> ORGANISM: Artificial
<220> FEATURE:
<223> OTHER INFORMATION: PCR primer sequence

<400> SEQUENCE: 3
atggctagcc acgcttgtgc ttttaatctg c                                  31

<210> SEQ ID NO 4
<211> LENGTH: 19
<212> TYPE: DNA
<213> ORGANISM: Artificial
<220> FEATURE:
<223> OTHER INFORMATION: Sense strand of Stathmin siRNA molecule

<400> SEQUENCE: 4
```

```
ggcacaaagg cgccaaatt                                              19

<210> SEQ ID NO 5
<211> LENGTH: 21
<212> TYPE: DNA
<213> ORGANISM: Artificial
<220> FEATURE:
<223> OTHER INFORMATION: Antisense strand of Stathmin siRNA molecule

<400> SEQUENCE: 5
uuuggcagcc auuugugcct c                                           21

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
agaccttcat agcgcacgtc at                                          22

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
cctcccsctg aacctgaaac                                             20

<210> SEQ ID NO 8
<211> LENGTH: 18
<212> TYPE: DNA
<213> ORGANISM: Artificial
<220> FEATURE:
<223> OTHER INFORMATION: PCR Primer

<400> SEQUENCE: 8
aggcgattaa gttgggta                                               18

<210> SEQ ID NO 9
<211> LENGTH: 18
<212> TYPE: DNA
<213> ORGANISM: Artificial
<220> FEATURE:
<223> OTHER INFORMATION: PCR Primer

<400> SEQUENCE: 9
cggtaggcgt gtacggtg                                               18

<210> SEQ ID NO 10
<211> LENGTH: 63
<212> TYPE: DNA
<213> ORGANISM: Artificial
<220> FEATURE:
<223> OTHER INFORMATION: Sequence encoding shRNA construct

<400> SEQUENCE: 10
aaggatcctg ctgttgacag tgagcgcttt ggcagccatt tgtgcctagt gaagccacag   60
atg                                                                63

<210> SEQ ID NO 11
<211> LENGTH: 60
<212> TYPE: DNA
```

```
<213> ORGANISM: Artificial
<220> FEATURE:
<223> OTHER INFORMATION: Sequence encoding shRNA construct

<400> SEQUENCE: 11
caaagcttcc gaggcagtag gcaatttggc agccatttgt gcctacatct gtggcttcac    60

<210> SEQ ID NO 12
<211> LENGTH: 63
<212> TYPE: DNA
<213> ORGANISM: Artificial
<220> FEATURE:
<223> OTHER INFORMATION: Sequence encoding shRNA construct

<400> SEQUENCE: 12
aaggatcctg ctgttgacag tgagcgcggc acaaatggct gccaaatagt gaagccacag    60
atg                                                                  63

<210> SEQ ID NO 13
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 13
caaagcttcc gaggcagtag gcaaggcaca aatggctgcc aaatacatct gtggcttcac    60

<210> SEQ ID NO 14
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 14
caaagcttcc gaggcagtag gcaaggcaca aatgtatgcc aaatacatct gtggcttcac    60

<210> SEQ ID NO 15
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 15
caaagcttcc gaggcagtag gcaaggcaca aatgtatgtc aaatacatct gtggcttcac    60

<210> SEQ ID NO 16
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 16
caaagcttcc gaggcagtag gcaaggcata aatgtatgtc aaatacatct gtggcttcac    60

<210> SEQ ID NO 17
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 17
```

```
caaagcttcc gaggcagtag gcaatttggc atacatttgt gcctacatct gtggcttcac      60

<210> SEQ ID NO 18
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 18
caaagcttcc gaggcagtag gcaatttgac atacatttgt gcctacatct gtggcttcac      60

<210> SEQ ID NO 19
<211> LENGTH: 60
<212> TYPE: DNA
<213> ORGANISM: Artificial
<220> FEATURE:
<223> OTHER INFORMATION: Sequence encoding shRNA construct

<400> SEQUENCE: 19
caaagcttcc gaggcagtag gcaatttgac atacatttat gcctacatct gtggcttcac      60

<210> SEQ ID NO 20
<211> LENGTH: 63
<212> TYPE: DNA
<213> ORGANISM: Artificial
<220> FEATURE:
<223> OTHER INFORMATION: Sequence encoding shRNA construct

<400> SEQUENCE: 20
aaggatcctg ctgttgacag tgagcgcggc acaaatgatt gccaaatagt gaagccacag      60
atg                                                                    63

<210> SEQ ID NO 21
<211> LENGTH: 63
<212> TYPE: DNA
<213> ORGANISM: Artificial
<220> FEATURE:
<223> OTHER INFORMATION: Sequence encoding shRNA construct

<400> SEQUENCE: 21
aaggatcctg ctgttgacag tgagcgcggt acaaatgatt gccaaatagt gaagccacag      60
atg                                                                    63

<210> SEQ ID NO 22
<211> LENGTH: 63
<212> TYPE: DNA
<213> ORGANISM: Artificial
<220> FEATURE:
<223> OTHER INFORMATION: Sequence encoding shRNA construct

<400> SEQUENCE: 22
aaggatcctg ctgttgacag tgagcgcggt acaaatgatt gacaaatagt gaagccacag      60
atg                                                                    63

<210> SEQ ID NO 23
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 23
aaggatcctg ctgttgacag tgagcgcggc acaaatggct gccaaatagt gaagccacag      60
```
atgtatttgg cagccatttg tgccttgcct actgcctcgg aagctttg        108

<210> SEQ ID NO 24
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 24
aaggatcctg ctgttgacag tgagcgcggc acaaatgatt gccaaatagt gaagccacag        60
atgtatttgg cagccatttg tgccttgcct actgcctcgg aagctttg        108

<210> SEQ ID NO 25
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 25
aaggatcctg ctgttgacag tgagcgcggt acaaatgatt gccaaatagt gaagccacag        60
atgtatttgg cagccatttg tgccttgcct actgcctcgg aagctttg        108

<210> SEQ ID NO 26
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 26
aaggatcctg ctgttgacag tgagcgcggt acaaatgatt gacaaatagt gaagccacag        60
atgtatttgg cagccatttg tgccttgcct actgcctcgg aagctttg        108

<210> SEQ ID NO 27
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 27
aaggatcctg ctgttgacag tgagcgcggc acaaatggct gccaaatagt gaagccacag        60
atgtatttgg catacatttg tgccttgcct actgcctcgg aagctttg        108

<210> SEQ ID NO 28
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 28
aaggatcctg ctgttgacag tgagcgcggc acaaatggct gccaaatagt gaagccacag        60
atgtatttga catacatttg tgccttgcct actgcctcgg aagctttg        108

<210> SEQ ID NO 29
<211> LENGTH: 108
<212> TYPE: DNA
<213> ORGANISM: Artificial
<220> FEATURE:
<223> OTHER INFORMATION: Sequence encoding shRNA construct -continued

```
<400> SEQUENCE: 29
aaggatcctg ctgttgacag tgagcgcggc acaaatggct gccaaatagt gaagccacag      60
atgtatttga catacattta tgccttgcct actgcctcgg aagctttg                 108

<210> SEQ ID NO 30
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 30
aaggatcctg ctgttgacag tgagcgcttt ggcagccatt tgtgcctagt gaagccacag      60
atgtaggcac aaatggctgc caaattgcct actgcctcgg aagctttg                 108

<210> SEQ ID NO 31
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 31
aaggatcctg ctgttgacag tgagcgcttt ggcagccatt tgtgcctagt gaagccacag      60
atgtaggcac aaatgtatgc caaattgcct actgcctcgg aagctttg                 108

<210> SEQ ID NO 32
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 32
aaggatcctg ctgttgacag tgagcgcttt ggcagccatt tgtgcctagt gaagccacag      60
atgtaggcac aaatgtatgt caaattgcct actgcctcgg aagctttg                 108

<210> SEQ ID NO 33
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 33
aaggatcctg ctgttgacag tgagcgcttt ggcagccatt tgtgcctagt gaagccacag      60
atgtaggcat aaatgtatgt caaattgcct actgcctcgg aagctttg                 108

<210> SEQ ID NO 34
<211> LENGTH: 108
<212> TYPE: DNA
<213> ORGANISM: Artificial
<220> FEATURE:
<223> OTHER INFORMATION: Sequence encoding shRNA construct

<400> SEQUENCE: 34
aaggatcctg ctgttgacag tgagcgcggc acaaatggct gccaaatagt gaagccacag      60
atgtatttgg cagccatttg tgccttgcct actgcctcgg aagctttg                 108

<210> SEQ ID NO 35
<211> LENGTH: 108
<212> TYPE: DNA
```

<213> ORGANISM: Artificial
<220> FEATURE:
<223> OTHER INFORMATION: Sequence encoding shRNA construct

<400> SEQUENCE: 35
aaggatcctg ctgttgacag tgagcgcggc acaaatgatt gccaaatagt gaagccacag    60
atgtatttgg cagccatttg tgccttgcct actgcctcgg aagctttg                108

<210> SEQ ID NO 36
<211> LENGTH: 23
<212> TYPE: DNA
<213> ORGANISM: Artificial
<220> FEATURE:
<223> OTHER INFORMATION: PCR Primer

<400> SEQUENCE: 36
tgagatctcc gaggcagtag gca                                            23

<210> SEQ ID NO 37
<211> LENGTH: 18
<212> TYPE: DNA
<213> ORGANISM: Artificial
<220> FEATURE:
<223> OTHER INFORMATION: PCR Primer

<400> SEQUENCE: 37
aggcgattaa gttgggta                                                  18

<210> SEQ ID NO 38
<211> LENGTH: 18
<212> TYPE: DNA
<213> ORGANISM: Artificial
<220> FEATURE:
<223> OTHER INFORMATION: PCR Primer

<400> SEQUENCE: 38
cggtaggcgt gtacggtg                                                  18

<210> SEQ ID NO 39
<211> LENGTH: 202
<212> TYPE: DNA
<213> ORGANISM: Artificial
<220> FEATURE:
<223> OTHER INFORMATION: Sequence encoding shRNA construct

<400> SEQUENCE: 39
ggatcctgct gttgacagtg agcgcggcac aaatggctgc caaatagtga agccacagat    60
gtatttggca gccatttgtg ccttgcctac tgcctcggag atcctgctgt tgacagtgag   120
cgcggcacaa atgattgcca aatagtgaag ccacagatgt atttggcagc catttgtgcc   180
ttgcctactg cctcggaagc tt                                            202

<210> SEQ ID NO 40
<211> LENGTH: 219
<212> TYPE: DNA
<213> ORGANISM: Artificial
<220> FEATURE:
<223> OTHER INFORMATION: Sequence encoding shRNA construct

<400> SEQUENCE: 40
ggatcctgct gttgacagtg agcgccgatt aactgtgaaa tgtatagtga agccacagat    60
gtacgattaa ctgtgaaatg tattgcctac tgcctcggtg ctgagctgga tgcttagatc   120
ctgctgttga cagtgagcgc cgattaacca agaaatgtat agtgaagcca cagatgtacg   180

```
attaactgtg aaatgtattg cctactgcct cggaagctt                      219
```

<210> SEQ ID NO 41
<211> LENGTH: 63
<212> TYPE: DNA
<213> ORGANISM: Artificial
<220> FEATURE:
<223> OTHER INFORMATION: PCR Primer

<400> SEQUENCE: 41

```
aaggatcctg ctgttgacag tgagcgccga ttaactgtga atgtatagt gaagccacag    60 atg                                                                63
```

<210> SEQ ID NO 42
<211> LENGTH: 60
<212> TYPE: DNA
<213> ORGANISM: Artificial
<220> FEATURE:
<223> OTHER INFORMATION: PCR Primer

<400> SEQUENCE: 42

```
caaagcttcc gaggcagtag gcaatacatt tcacagttaa tcgtacatct gtggcttcac    60
```

<210> SEQ ID NO 43
<211> LENGTH: 63
<212> TYPE: DNA
<213> ORGANISM: Artificial
<220> FEATURE:
<223> OTHER INFORMATION: PCR Primer

<400> SEQUENCE: 43

```
aaggatcctg ctgttgacag tgagcgccga ttaaccaaga atgtatagt gaagccacag    60 atg                                                                63
```

<210> SEQ ID NO 44
<211> LENGTH: 22
<212> TYPE: DNA
<213> ORGANISM: Artificial
<220> FEATURE:
<223> OTHER INFORMATION: PCR Primer

<400> SEQUENCE: 44

```
aaggatcctg ctgttgacag tg                                           22
```

<210> SEQ ID NO 45
<211> LENGTH: 21
<212> TYPE: DNA
<213> ORGANISM: Artificial
<220> FEATURE:
<223> OTHER INFORMATION: PCR Primer

<400> SEQUENCE: 45

```
caaagcttcc gaggcagtag g                                            21
```

<210> SEQ ID NO 46
<211> LENGTH: 40
<212> TYPE: DNA
<213> ORGANISM: Artificial
<220> FEATURE:
<223> OTHER INFORMATION: PCR Primer

<400> SEQUENCE: 46

```
tgagatctaa gcatccagct cagcaccgag gcagtaggca                        40
```

<210> SEQ ID NO 47

```
<211> LENGTH: 18
<212> TYPE: DNA
<213> ORGANISM: Artificial
<220> FEATURE:
<223> OTHER INFORMATION: PCR Primer

<400> SEQUENCE: 47
aggcgattaa gttgggta                                                18

<210> SEQ ID NO 48
<211> LENGTH: 18
<212> TYPE: DNA
<213> ORGANISM: Artificial
<220> FEATURE:
<223> OTHER INFORMATION: PCR Primer

<400> SEQUENCE: 48
cggtaggcgt gtacggtg                                                18

<210> SEQ ID NO 49
<211> LENGTH: 3661
<212> TYPE: DNA
<213> ORGANISM: Homo sapiens

<400> SEQUENCE: 49
ttagtcagct tcagtctcgt cagcagggtc tttggattct tgttcttcc gcacttcttc     60 aatgtgctta tcctgtaaag gaagggtaag gtgtcatcag tcaaaaaaaa aaaaaaaaa    120 aaaagcctgt caagtcacga cccccagccc ccacctcaaa gaggcccaac acaacctcag   180
tgcatatatt acagcctgtg ggaaccacac aatttaagtt ctgagacatc atcatcaaat   240
ctcctgggtc ccttgtagaa cctaacaagc tgcctactgg acttccaagg actgtgcaat   300
tatgctggga attactgaat attccatctt aaaatatacc tttcatttaa tatgttaagc   360
cccaaaatgg atgacaaaaa gacaccaaac acctttatc aaagcactta gttcaagcca    420
actcattggt gcatcaaact ccaagctcaa ccctttaca aagtaagaaa ccaaccttct    480
ctcgcaaacg ttccagtttg gcagccattt gtgcctctcg ttctctttta ttagcttcca   540
ttttgtgggt cagtttctct tctgccattt tactgaagtt gttgttctct tctattgcct   600
tctgaagcac ttcttttctcg tgctctcgtt tctcagccag ctgcttcaag acctcagctt   660
catgggactg gaaaaaaaag tttaataggc taggcactct aaaatgtatt caggctgggt   720
gtggtggctc acgcctgtaa tcccagcact tgggaggcc aaggtgggtg gatcatttga    780
ggtcaggagt tcaagaccag cctggccaac atggtgaaat cctacctata ctaaaaatac   840
aaaaattagc cgggcgtggt ggcgggtgcc tgtagtctaa gttacttggg aggctgaggc   900
agaagaattg cttgaacccg ggaggtggag gttgcagtga actgagatcg tgccactgca   960
ctccaccctg ggtgacagag actctgcctc aaaaaataaa atgtattcag cataagttaa  1020
aattacaata aaaataattt actaagggga ttgaaaaggg gcagaaaata aggtcccttt   1080
aaataacacc aaaattagga cctgaattat ccctatcata aaatactgtg aaaatgatat   1140 tcttttttcta gtatttgtat ttaactttgg aaaagtgctt atctgttcag aaatcttacc  1200
caattagtcc ttaaggaaat ccttgtaaga tttactgctt aatggtatct ggatgacttg   1260
aggaatatgt acttgcgagt ggcacttta ttgtaaagaa tttcactatt taacttcaaa    1320
agctacccaa agaaaactag ctcattgtaa aaattttaac cataactgat aaaacaatga   1380
taggaaattc aagactaagt ctgtagatta ctatttaaga cagaaaaatt tgtttcaagg   1440
aaaaggctta ttagcttttg tctcaggaaa ctgcattaat taccagacca taccttggta   1500
```

-continued

```
tgaccccttc aacagaacag cttgttctca aaacacattg gaaccactga cttgcaggat      1560
aaccacagag catctgacac tggttctatt gattctcttc tgccaaatcc tagtcatgat      1620
gggagtttca ttatatttag ccagttacta tgtaaagcac aggctaatga ctacagggcc      1680
agggttgatg tctaaaaagc tttccactgt ccaacctttg gttgtattgc ttcctcctac      1740
tccatgaact cacactattg catagaagac gactccttag tgtaagcact gaggctcttc      1800
gggcgggtgt gtgtgtatac tacaaatcac tatgctggtc tggggaaggt tattaccttt      1860 cctttgtgc ctcacttgcc ccagctttaa aatcaatcct atcagggttg ttgagaaagg       1920
gagttaaatg aaaagttatg tacagttgtt aatgagtaac attgaatgga aagaaacaca      1980
ccaaaatgtt aacactggtt gcttctcgga agcgggataa tgaatacttt taatttccat      2040
ttataaattt ctgtatttcc caaattttct acaactagca tattaatatt tattgattct      2100
tctgattagc ttttaaagat agttacttta aatagaatt gtttagataa gagaaaagct       2160
accatgatac cagctgagca acacaatcac actagcaatt taaaatgtta ttgtacagct      2220
ctcaaaaaac aaaaccaaag tgccaaagaa tcatctggca acaaatcttt tcaaagagga      2280
agcatgagag aagcatgagc tttggtttaa gatagaccag ggcttgaatt ctgaccccaa      2340
cacttactag ttgtatgact gcagaaaaac gacttaacat tcctgaaact gtttctaatt      2400
tccattattt gaggcaacac catgtattaa aggagaaaaa tataaacaaa ggagcgggca      2460
tgtaacagga gttcaataaa tgaggactgg tatttccttc cagtcactgg catatgtaat      2520
aatcacagtg tagctacaat tctgttttct tcctgttata gaaataaaat tgatctgccc      2580
attacataaa ttaatatcct gctttctgtg aattgcttcg tttaccttgc gtctttcttc      2640
tgcagcttct aatttcttct gaatttcctc cagggaaaga tccttcttct ttggagggga      2700 aaggggggaat tctggaacag attcttttga ccgagggctg agaatcagct caaaagcctg      2760
gcctgaggca cgcttctcca gttctttcac ctggatatct agaattgatt atatttataa      2820
ttcagaaaac caggattctc ctgttctaat aaactgtact ataattttct aaaacccaaa      2880
tcaatttaat gtattaaact agggctgatg aggaaagttg tgttttttt ccccttttta       2940 ttcctatcag tctactgaca ctaggggaag atgtatttgc aggcaagata ttattatcta      3000
aataccattt cccaaggcca ggtaccatgg ctcatgccta taatcccagc accgtgggag      3060
gccaacatgg gaagatccct tgagccctga agtttgagac cagcctgggc aacaaaggga      3120
aagcccatct ctacaaaaaa aattttttt gattaggtgg gtgtggtggc ccatgtcgat       3180
agtcccagat gctatggagg ctgaggtggg agaatcgctt gagcccactt gagctccaga     3240
agtcaaggct gcaatgagct ataattaagc cactgcactc cagcctgggc aacaaggtga      3300
gaccctgtct caaaaaaaat aaaaaccatc tcccagaaaa acaaagctca acattttgg       3360 attaataaat actgttttga gacatcagta tctgacaatc gctttcataa acaaaagact      3420
tgtgcaaact ccacaatttt gcttcagact aagccaaact gtccaataaa caattacgag      3480
ctctcggcac attcaagtga taatcatttt taaattcttc tcctattcat aaaataggtt      3540
ttggtaagac caaaacataa gtgccaaatc aaaggcgaag acctgagcca tctcaatcta      3600
aaatcataag cccattacaa tttcagattt tccaaataga ttacctacca gaagaagcca      3660
t                                                                     3661
```

<210> SEQ ID NO 50
<211> LENGTH: 1542
<212> TYPE: RNA
<213> ORGANISM: Homo sapiens

```
<400> SEQUENCE: 50
gcucucggcc aaugcggagc cccgcgcgga ggucacgugc cucuguuugg cgcuuuugug        60
cgcgcccggg ucuguuggug cucagagugu ggucaggcgg cucggacuga gcaggacuuu       120
ccuuauccca guugauugug cagaauacac ugccugucgc uugucuucua uuccaccaugg      180 cuucuucuga uauccaggug aaagaacugg agaagcgugc cucaggccag gcuuuugagc       240
ugauucucag cccucgguca aaagaaucug uuccagaauu cccccuuucc ccuccaaaga       300
agaaggaucu uucccuggag gaaauucaga agaaauuaga agcugcagaa gaaagacgca       360
agucccauga agcuggagguc uugaagcagc uggcugagaa acgagagcac gagaaagaag      420
ugcuucagaa ggcaauagaa gagaacaaca acuucaguaa aauggcagaa gagaaacuga      480
cccacaaaau ggaagcuaau aaagagaacc gagaggcaca aauggcugcc aaacuggaac      540
guuugcgaga gaaggauaag cacauugaag aagugcggaa gaacaaagaa uccaaagacc     600
cugcugacga gacugaagcu gacuaauuug uucugagaac ugacuuucuc cccauccccu     660
uccuaaauau ccaaagacug uacuggccag ugucauuuua uuuuuucccu ccugacaaau     720
auuuuagaag cuaauguagg acuguauagg uagauccaga uccagacugu aagauguugu      780
uuuaggggcu aaaggggaga aacugaaagu guuuuacucu uuuucuaaag uguuggucuu       840
ucuaauguag cuauuuuucu uguugcaucu uuucuacuuc aguacacuug guguacuggg      900
uuaauggcua guacuguauu ggcucuguga aaacauauuu gugaaaagag uauguagugg       960
cuucuuuuga acuguuagau gcugaauauc uguucacuuu ucaaucccaa uucugucccaa     1020 aucuuaccag augcuacugg acuugaaugg uuaauaaaac ugcacagugc uguuggugg      1080 agugacuucu uuugaguuag guuaauaaau caagccauag agccccuccu gguugauacu      1140
uguuccagau gggcucuuug gggcuggaug aaauacccaa cgcacaaaug accgcacguu     1200
cucugccccg uuucuugccc cagugugguu ugcauugucu ccuuccacaa ugacugcuuu     1260
guuuggaugc cucagcccag gucagcuguu acuuucuuuc agauguuuau uugcaaacaa     1320
ccauuuuuug uucuguguccс cuuuuaaaag gcagauuaaa agcacaagcg uguuucuaga      1380
gaacaguuga gagagaaucu caagauucua cuugguggu ugcuugcucu acguuacagg      1440
uggggcaugu ccucauccuu uccugccaua aaagcuauga cacgagaauc agaauauuaa      1500
uaaaacuuua uguacugcug uagcaaaaaa aaaaaaaaaa aa                        1542
```